(12) United States Patent
Friis et al.

(10) Patent No.: US 12,120,959 B2
(45) Date of Patent: Oct. 15, 2024

(54) STACKED PIEZOELECTRIC ENERGY HARVESTER

(71) Applicants: UNIVERSITY OF KANSAS, Lawrence, KS (US); EVOKE MEDICAL, LLC, Lawrence, KS (US)

(72) Inventors: Elizabeth Annamaria Friis, Lawrence, KS (US); Ember Krech, Lawrence, KS (US); Eileen Cadel, Lawrence, KS (US); Bonnie Reinsch, Lawrence, KS (US); Leighton Lapierre, Thornton, CO (US)

(73) Assignees: UNIVERSITY OF KANSAS, Lawrence, KS (US); EVOKE MEDICAL, LLC, Lawrence, KS (US)

( * ) Notice: Subject to any disclaimer, the term of this patent is extended or adjusted under 35 U.S.C. 154(b) by 514 days.

(21) Appl. No.: 17/045,262

(22) PCT Filed: Apr. 2, 2019

(86) PCT No.: PCT/US2019/025352
§ 371 (c)(1),
(2) Date: Oct. 5, 2020

(87) PCT Pub. No.: WO2019/195264
PCT Pub. Date: Oct. 10, 2019

(65) Prior Publication Data
US 2021/0367134 A1  Nov. 25, 2021

Related U.S. Application Data

(60) Provisional application No. 62/653,830, filed on Apr. 6, 2018.

(51) Int. Cl.
*H10N 30/50* (2023.01)
*H10N 30/30* (2023.01)
(Continued)

(52) U.S. Cl.
CPC .............. *H10N 30/50* (2023.02); *H10N 30/30* (2023.02); *H10N 30/8536* (2023.02);
(Continued)

(58) Field of Classification Search
CPC ...... H02N 2/186; H02N 2/185; A61N 1/0551; H10N 30/857; H10N 30/8554; H10N 30/8536; H10N 30/50; H10N 30/30
See application file for complete search history.

(56) References Cited

U.S. PATENT DOCUMENTS

| 6,143,035 A | 11/2000 | McDowell |
| 2006/0015184 A1 | 1/2006 | Winterbottom et al. |

(Continued)

FOREIGN PATENT DOCUMENTS

CN   107749721   2/2018

OTHER PUBLICATIONS

Feenstra, J., Granstrom, J., and Sodano, H., "Energy Harvesting through a Backpack Employing a Mechanically Amplified Piezoelectric Stack," Mechanical Systems and Signal Processing, 22(3), pp. 721-734 (2008).

(Continued)

*Primary Examiner* — J. San Martin
*Assistant Examiner* — Jaydi San Martin
(74) *Attorney, Agent, or Firm* — MEDLER FERRO WOODHOUSE & MILLS PLLC

(57) ABSTRACT

The present application relates to stacked piezoelectric energy harvesters that include compliant layers between piezoelectric layers. The energy harvesters are useful in various structures and devices, including tissue-stimulating implants, such as spinal fusion implants. The present application also relates to methods of increasing the power output of a piezoelectric energy harvester through the inclusion of compliant layers.

20 Claims, 26 Drawing Sheets

(51) Int. Cl.
*H10N 30/853* (2023.01)
*H10N 30/857* (2023.01)
*A61N 1/05* (2006.01)

(52) U.S. Cl.
CPC ....... *H10N 30/8554* (2023.02); *H10N 30/857* (2023.02); *A61N 1/0551* (2013.01)

(56) References Cited

U.S. PATENT DOCUMENTS

| | | | | |
|---|---|---|---|---|
| 2006/0113878 | A1* | 6/2006 | Pei | H10N 30/87 |
| | | | | 310/363 |
| 2015/0134061 | A1 | 5/2015 | Friis et al. | |
| 2016/0346556 | A1* | 12/2016 | Slepian | H10N 30/30 |
| 2019/0068086 | A1* | 2/2019 | Khizroev | H10N 35/80 |

OTHER PUBLICATIONS

Howells, C. A., "Piezoelectric Energy Harvesting," Energy Conversion and Management, 50(7), pp. 1847-1850 (2009).

Goetzinger, N. C.; Tobaben, E. J.; Domann, J. P.; Arnold, P. M.; Friis, E. A. Composite piezoelectric spinal fusion implant: Effects of stacked generators. J. Biomed. Mater. Res. B Appl. Biomater. 104, 158-164 (2016).

Tobaben, E. J.; Goetzinger, N. C.; Domann, J. P.; Barrett-Gonzalez, R.; Arnold, P. M.; Friis, E. A. Stacked macro fiber piezoelectric composite generator for a spinal fusion implant. Smart Mater. Struct. 24 (2015).

Kiran et al., "Poling direction driven large enhancement in piezoelectric performance," Scripta Materialia 151:76-81 (2018).

* cited by examiner

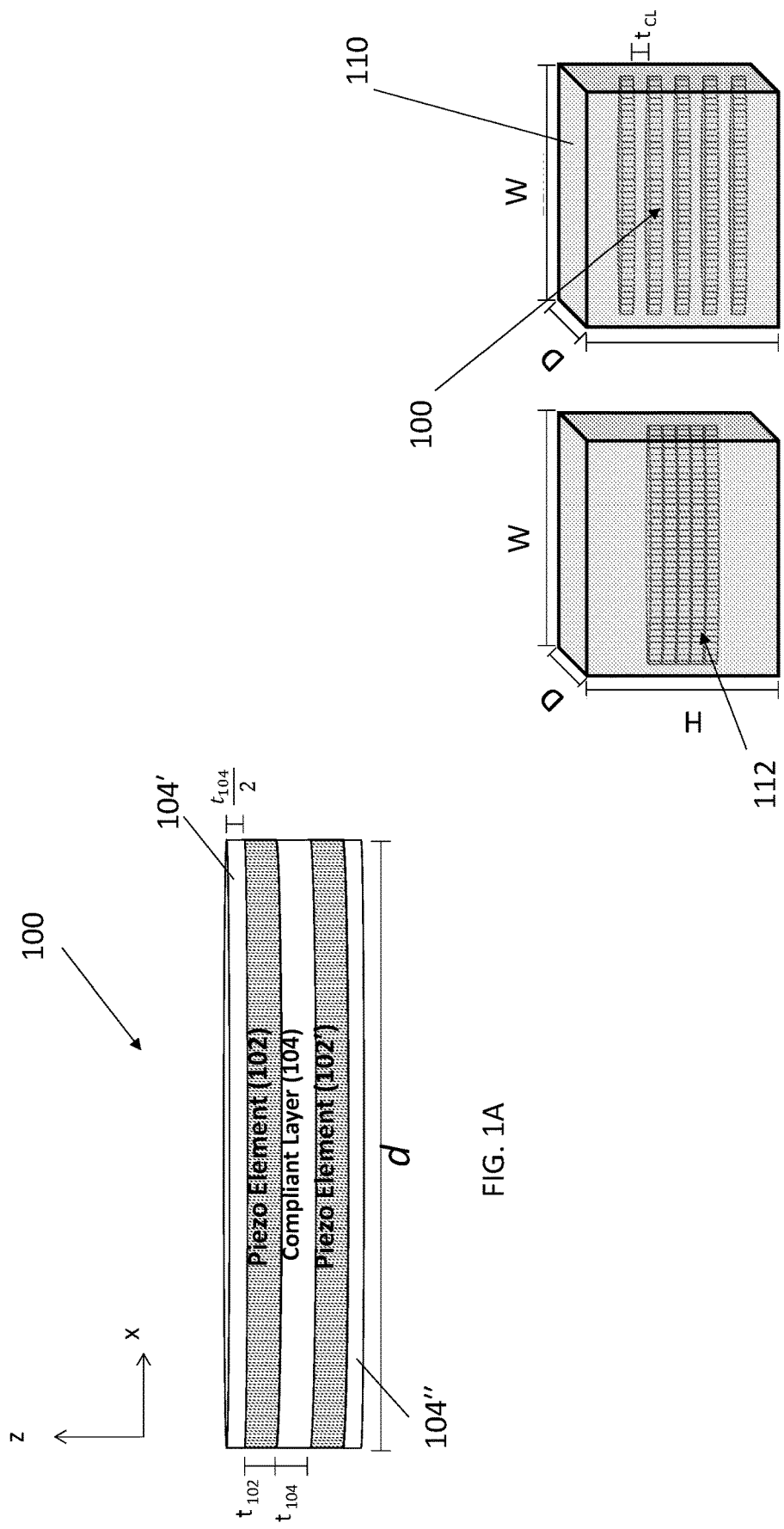

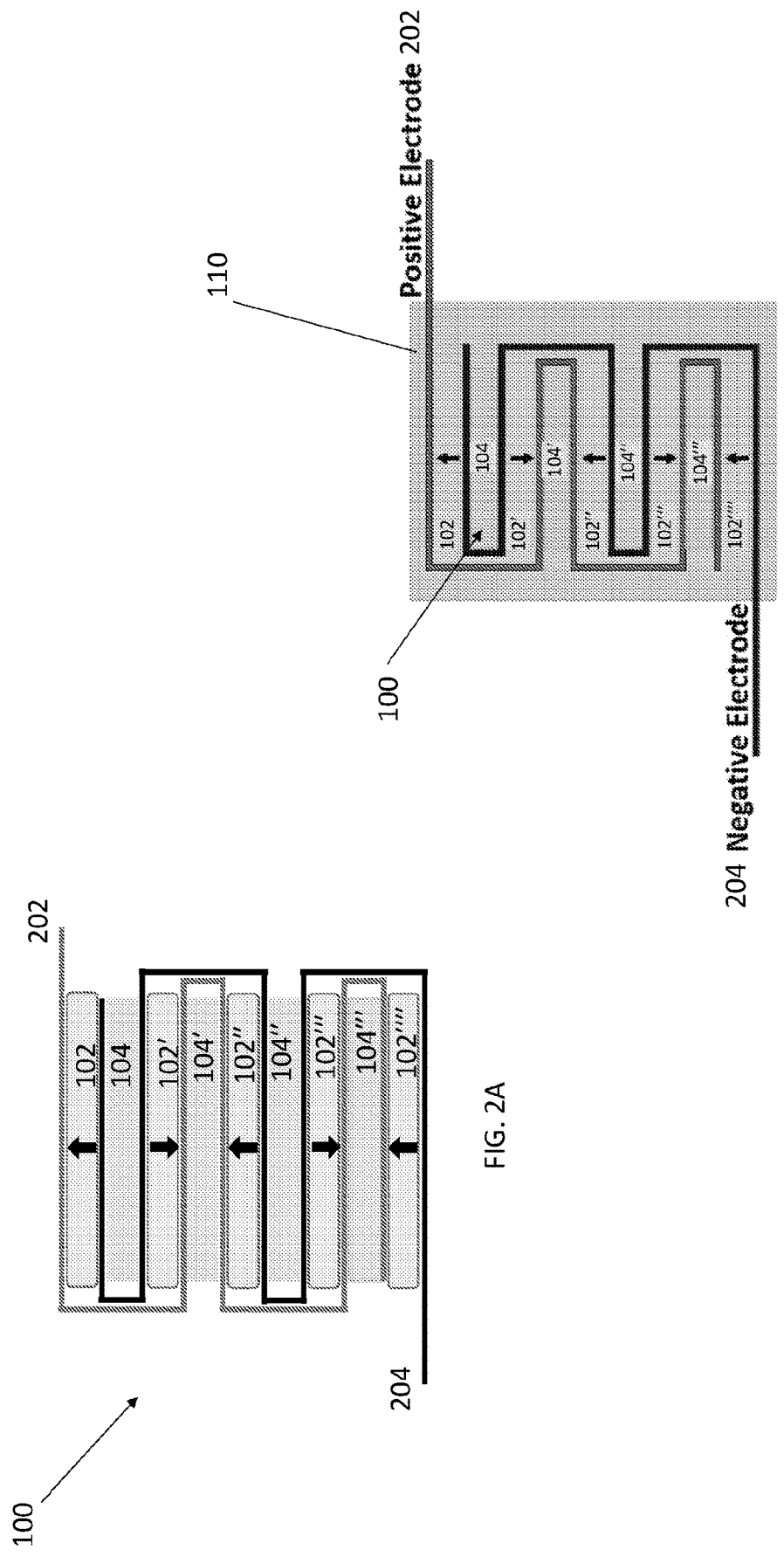

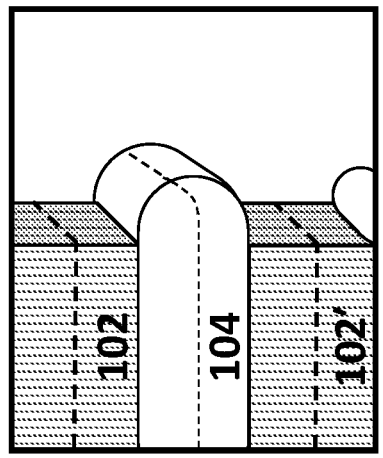
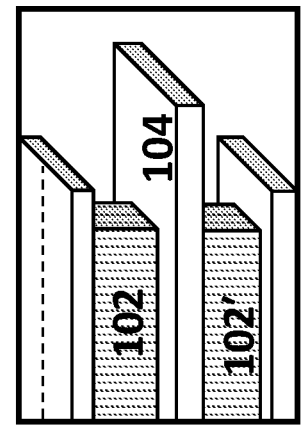
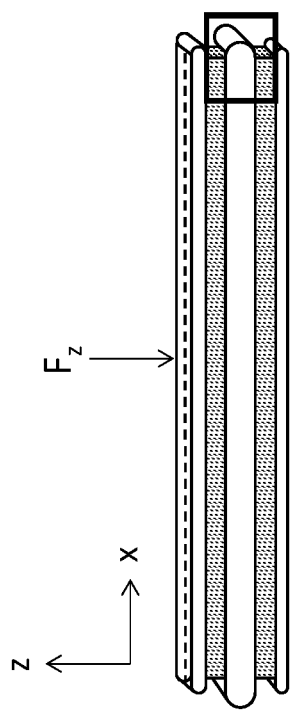
FIG. 3A
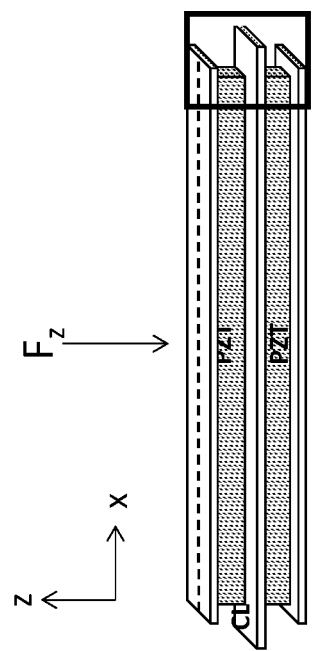
FIG. 3B

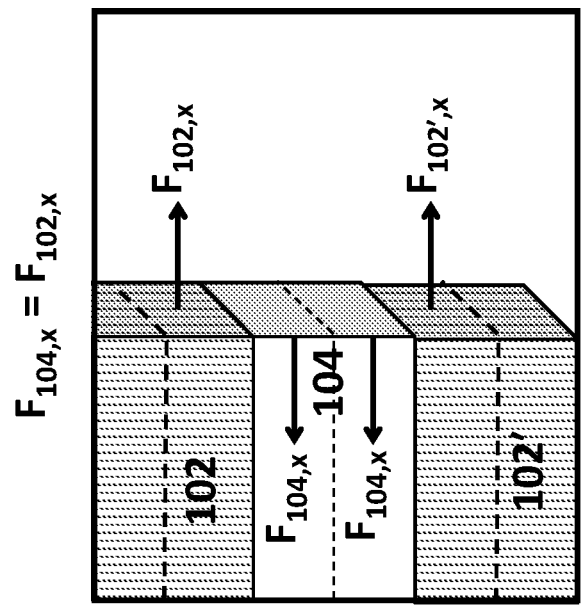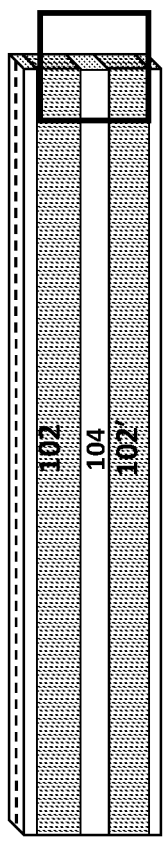
FIG. 3C

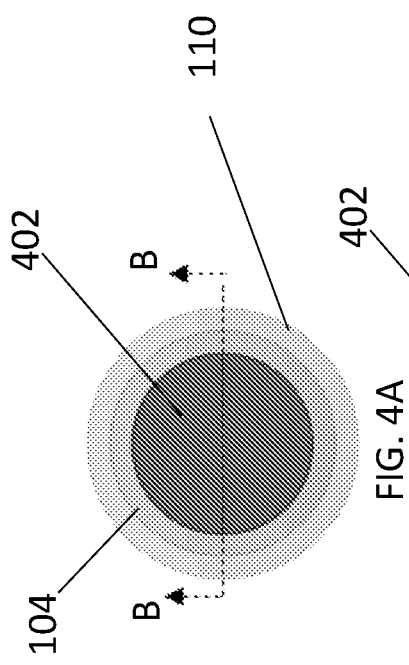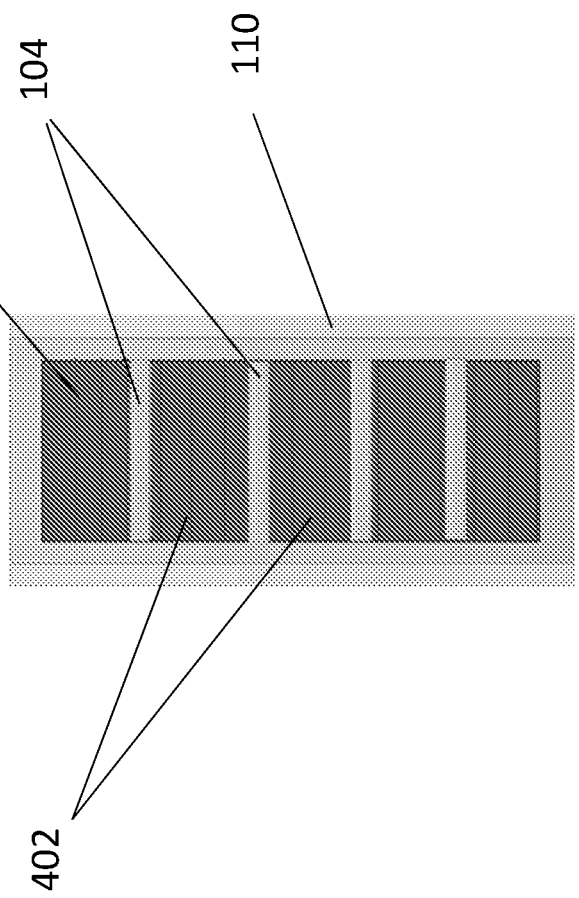

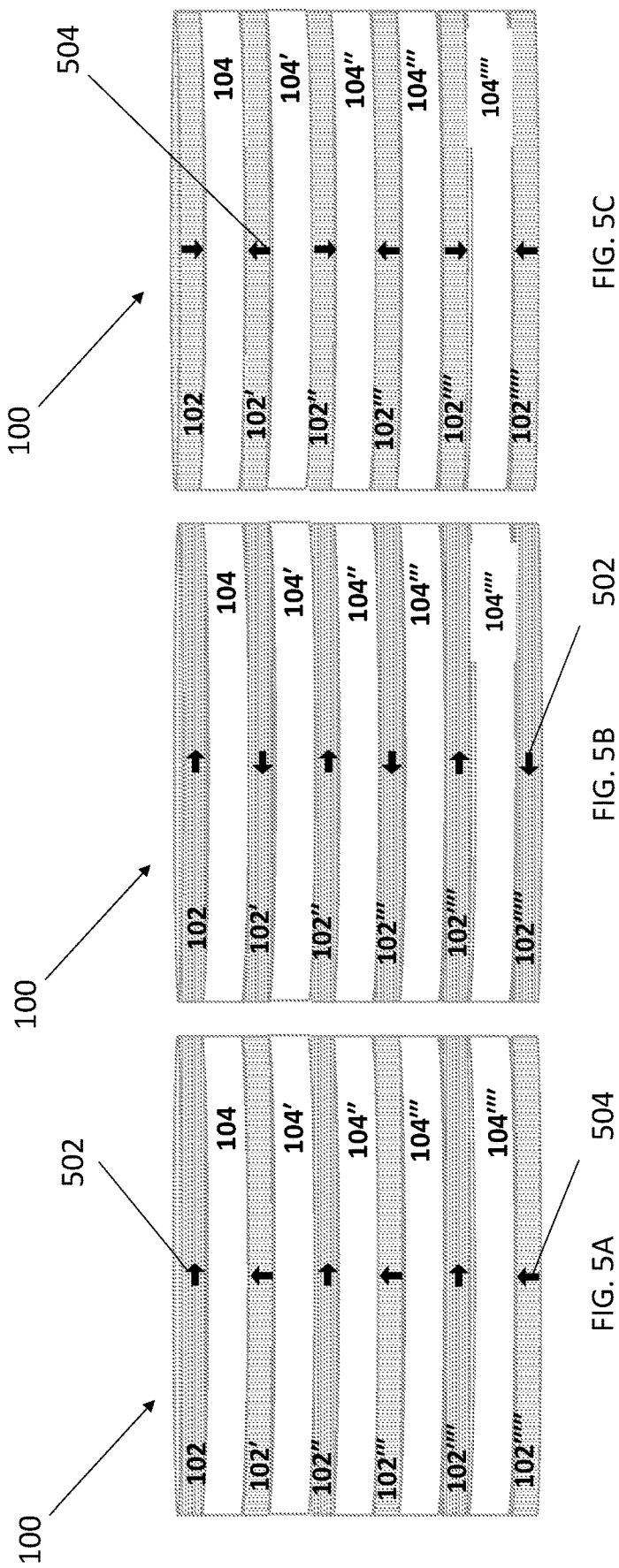

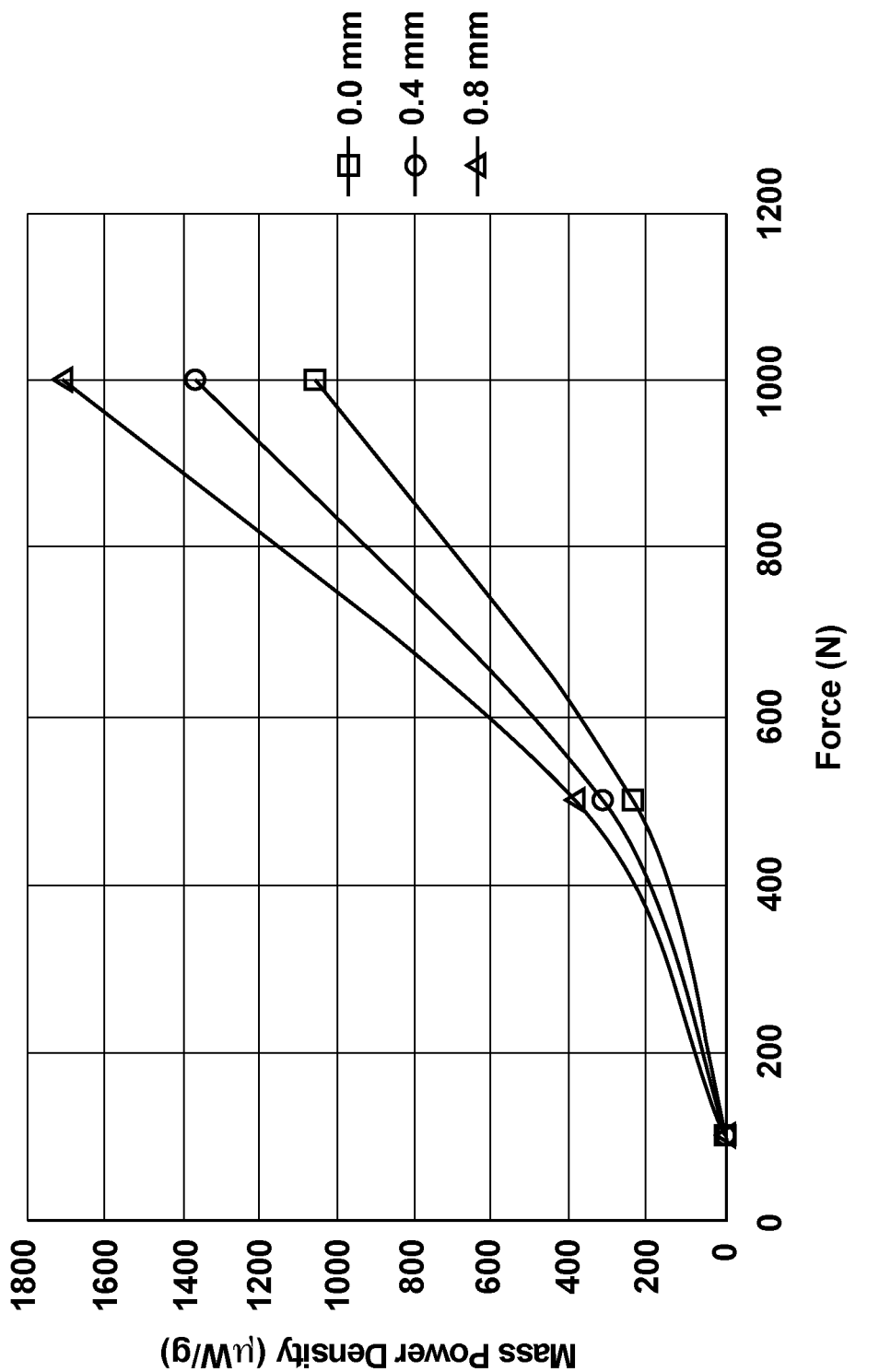

STACKED PIEZOELECTRIC ENERGY HARVESTER

STATEMENT REGARDING FEDERALLY-SPONSORED RESEARCH AND DEVELOPMENT

This invention was made with government support under grant no. AR070088 awarded by the National Institutes of Health. The government has certain rights in the invention.

BACKGROUND OF THE INVENTION

Field of the Invention

The present application relates to stacked piezoelectric energy harvesters that include compliant layers between piezoelectric layers. The energy harvesters are useful in various structures and devices, including tissue-stimulating implants, such as spinal fusion implants, as well as other fields including civil infrastructure, automotive applications, and other areas where energy harvesting is desired from a piezoelectric structure. The present application also relates to methods of increasing the power output of a piezoelectric energy harvester through the inclusion of compliant layers.

Background of the Invention

Piezoelectric elements can be effective energy harvesters, but are most efficient when the device matches both the electrical and mechanical impedances of the loading conditions [Feenstra, J., Granstrom, J., and Sodano, H., 2008, "Energy Harvesting through a Backpack Employing a Mechanically Amplified Piezoelectric Stack," *Mechanical Systems and Signal Processing*, 22(3), pp. 721-734]. At low frequencies, the mismatch in device resonance frequency and loading frequency amplifies the limited charge density and strain amplitude, making them less effective [Jaffe, B., Cook jr., W. R., and Jaffe, H., 197], "CHAPTER 12—APPLICATIONS OF PIEZOELECTRIC CERAMICS," Piezoelectric Ceramics, Academic Press, pp. 271-2801. Most of the research done on piezoelectric devices to overcome this suboptimal performance at low frequencies has been by modifying materials, mounting design configurations, and manufacturing processes in bimorph beams [see, e.g., Howells, C. A., 2009, "Piezoelectric Energy Harvesting," *Energy Conversion and Management*, 50(7), pp. 1847-1850.]

Piezoelectric stacks are used to lower source impedance and increase functionality at lower resistances [Platt, S. R., Farritor, S., and Haider, H., 2005, "On Low-Frequency Electric Power Generation with PZT Ceramics," *IEEE/ASME Transactions on Mechatronics*, 10(2), pp. 240-252.] and have been used in several studies to harvest energy from low frequency motion [see id.].

To date, little work has been done to increase efficiency of power generation utilizing piezoelectric stacks.

SUMMARY OF PREFERRED EMBODIMENTS

The present study presents a manufacturing method for piezoelectric energy harvesters that include piezoelectric elements stacked with compliant layers. This method results in an energy harvester that provides increased power generation and increased durability for use in various applications, including tissue stimulating implants such as spinal implants as well as other fields including civil infrastructure, automotive applications, and other areas where energy harvesting is desired from a piezoelectric structure.

The present application provides a stacked piezoelectric energy harvester, comprising: a first piezoelectric element layer; a first compliant layer positioned adjacent the first piezoelectric element layer; and a second piezoelectric element layer positioned adjacent the first compliant layer, wherein a ratio of a volume of the first piezoelectric element layer and/or a volume of the second piezoelectric element layer, to a volume of the first compliant layer is between about 1:8 to about 8:1 (volume piezoelectric:volume compliant), or wherein a ratio of a thickness of the first piezoelectric element layer and/or a thickness of the second piezoelectric element layer, to a thickness of the first compliant layer is between about 1:8 to about 8:1 (thickness piezoelectric:thickness compliant).

In further embodiments, provided is a stacked piezoelectric energy harvester, comprising: alternating layers of: N compliant layers; and N−1 piezoelectric element layers; wherein the compliant layers and the piezoelectric element layers are adjacent one another, wherein N is a whole integer between 3 and 20, and wherein a ratio of a volume of at least one of the piezoelectric element layers, to a volume of at least one of the compliant layers is between about 1:8 to about 8:1 (volume piezoelectric:volume compliant), or wherein a ratio of a thickness of at least one of the piezoelectric element layers, to a thickness of at least one of the compliant layers is between about 1:8 to about 8:1 (thickness piezoelectric:thickness compliant).

Also provided herein is a method of increasing the power production of a stacked piezoelectric energy harvester having two or more piezoelectric element layers, comprising layering a compliant layer between each piezoelectric element layer of the energy harvester, wherein a ratio of a volume of at least one of the piezoelectric element layers, to a volume of at least one of the compliant layers is between about 1:8 to about 8:1 (volume piezoelectric:volume compliant), or wherein a ratio of a thickness of at least one of the piezoelectric element layers, to a thickness of at least one of the compliant layers is between about 1:8 to about 8:1 (thickness piezoelectric:thickness compliant).

In additional embodiments, provided herein is a method of providing power generation from a stacked piezoelectric energy harvester described herein, comprising loading the stacked piezoelectric energy harvester with a load of at least about 100 N.

Further embodiments, features, and advantages of the embodiments, as well as the structure and operation of the various embodiments, are described in detail below with reference to accompanying drawings.

BRIEF DESCRIPTION OF THE FIGURES

FIG. 1A shows an exemplary stacked piezoelectric energy harvester, in accordance with embodiments herein.

FIG. 1B show a traditional piezoelectric stack and an exemplary stacked piezoelectric energy harvester including compliant layers, both encapsulated, in accordance with embodiments herein.

FIG. 2A shows an exemplary stacked piezoelectric energy harvester, including electrical connections, in accordance with embodiments hereof.

FIG. 2B shows an encapsulated exemplary stacked piezoelectric energy harvester, including electrical connections, in accordance with embodiments hereof.

FIGS. 3A-3D illustrate exemplary mechanisms for enhanced power production provided by the stacked piezoelectric energy harvesters described herein.

FIGS. 4A and 4B illustrate a stacked piezoelectric energy harvester including groupings of piezoelectric monolayers, in accordance with embodiments hereof.

FIGS. 5A-5C show exemplary poling directions of piezoelectric element layers in stacked piezoelectric energy harvesters in accordance with embodiments hereof.

FIG. 18 shows average mass power density of each of the CLACS groups with respect to load applied (5 Hz, 2.5 MΩ).

DETAILED DESCRIPTION OF PREFERRED EMBODIMENTS

Figure 3D:
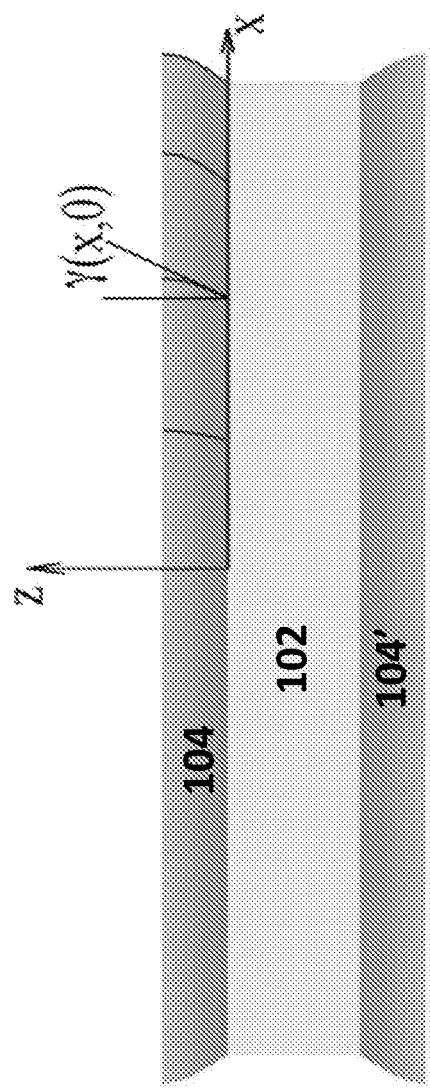

It should be appreciated that the particular implementations shown and described herein are examples and are not intended to otherwise limit the scope of the application in any way.

The published patents, patent applications, websites, company names, and scientific literature referred to herein are hereby incorporated by reference in their entireties to the same extent as if each was specifically and individually indicated to be incorporated by reference. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of the latter.

As used in this specification, the singular forms "a," "an" and "the" specifically also encompass the plural forms of the terms to which they refer, unless the content clearly dictates otherwise. The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

Technical and scientific terms used herein have the meaning commonly understood by one of skill in the art to which the present application pertains, unless otherwise defined.

Reference is made herein to various methodologies and materials known to those of ordinary skill in the art.

In embodiments, provided herein is a stacked piezoelectric energy harvester. The term "stacked" when describing an energy harvester herein refers to the use of a plurality of elements or layers, positioned adjacent one another. An "energy harvester" refers to a structure that can derive, store and/or transmit power that has been generated from a source. In the embodiments described herein, the source is a piezoelectric, resulting in a piezoelectric energy harvester. As used herein, "plurality" refers to 2 or more, suitably 5 or more, 10 or more, 50 or more, 100 or more, 500 or more, 1000 or more, etc., of an item.

As used herein, a "piezoelectric" is a material that is capable of generating a voltage when a mechanical force is applied to the material. As used herein, a "piezoelectric element" refers to a formed material (i.e. material having a particular shape and dimensions) that is capable of generating a voltage when a mechanical force is applied to the material. A "piezoelectric element layer" refers to any material with piezoelectric properties that is arranged in, formed in, or otherwise a component of, a structure that can be used as a layer in a stack as described herein.

In embodiments, for example as shown in FIG. 1A, a stacked piezoelectric energy harvester 100 is provided (also called "stack" herein), which includes a first piezoelectric element layer 102, a first compliant layer 104 positioned adjacent first piezoelectric element layer 102, and a second piezoelectric element layer 102' positioned adjacent first compliant layer 104.

As shown in FIG. 1A, suitably the piezoelectric element layers and compliant layers are placed adjacent each other such that a large surface area of each is placed adjacent the other (i.e., the larger surface area rather than the thinner edges of the layers). Layers are positioned "adjacent" each other when they are in close proximity to each other, suitably with either no intervening material or a small amount of adhesive or glue between the other layers.

The exemplary stacked piezoelectric energy harvester 100 shown in FIG. 1A includes two piezoelectric element layers 102 and 102', as well as three compliant layers 104, 104', 104". It should be noted that the addition of compliant layers 104' and 104" is shown to illustrate an exemplary method of stacking additional layers, and is not limiting with regard to the number, thickness (t) or orientation of any of the layers in preparing the stacked piezoelectric energy harvesters described herein.

As used herein, a "compliant" layer refers to a layer of material, suitably polymeric, that acts as a spacer or separation layer between two adjacent piezoelectric element layers, and/or as outer layers of a stacked piezoelectric energy harvester. Compliant layers utilized in the stacks herein provide a toughened structure to the stacks and increase power generation, as described herein.

In exemplary embodiments, a ratio of a volume of the first piezoelectric element layer and/or a volume of the second piezoelectric element layer, to a volume of the first compliant layer is between about 1:8 to about 8:1 (volume piezoelectric:volume compliant). That is, the volume of one piezoelectric element layer compared to the volume of one compliant layer is between about 1:8 to about 8:1 (volume piezoelectric:volume compliant). The respective volumes of a piezoelectric layer and a compliant layer making up the stacks described herein can be routinely determined using geometric measurements, or otherwise calculated if a non-uniform shaped layer is utilized. It should be noted that volumes of one or more piezoelectric element layers compared to one or more compliant layers, can be different than each other and can vary within the ratio range of about 1:8 to about 8:1. In suitable embodiments, the volume of one piezoelectric element layer compared to one compliant layer is between about 1:8 to about 8:1 (volume piezoelectric:volume compliant), more suitably about 1:2 to about 1:10, or about 1:3 to about 1:9, about 1:4 to about 1:8, about 1:5 to about 1:7, or 1:8 to about 7:1, about 1:8 to about 6:1, about 1:8 to about 5:1, about 1:8 to about 4:1, about 1:8 to about 3:1, about 1:8 to about 2:1, about 1:8 to about 1:1, or about 1:4, about 1:5, about 1:6, about 1:7 or about 1:8 (volume piezoelectric:volume compliant).

In additional embodiments, a ratio of a thickness of the first piezoelectric element layer and/or a thickness of the second piezoelectric element layer, to a thickness of the first compliant layer is between about 1:8 to about 8:1 (thickness piezoelectric:thickness compliant). That is, the thickness of one piezoelectric element layer compared to one compliant layer is between about 1:8 to about 8:1 (thickness piezoelectric:thickness compliant). The respective thicknesses of a piezoelectric layer and a compliant layer making up the stacks described herein can be routinely determined using geometric measurements. It should be noted that thicknesses of one or more piezoelectric element layers compared to one or more compliant layers, can be different than each other and can vary within the ratio range of about 1:8 to about 8:1. In suitable embodiments, the thickness of one piezoelectric element layer compared to one compliant layer is between about 1:8 to about 8:1 (thickness piezoelectric:thickness compliant), more suitably about 1:2 to about 1:10, or about 1:3 to about 1:9, about 1:4 to about 1:8, about 1:5 to about 1:7, or 1:8 to about 7:1, about 1:8 to about 6:1, about 1:8 to about 5:1, about 1:8 to about 4:1, about 1:8 to about 3:1, about 1:8 to about 2:1, about 1:8 to about 1:1, or about 1:4, about 1:5, about 1:6, about 1:7 or about 1:8 (thickness piezoelectric:thickness compliant).

In embodiments, both the ratios of the thicknesses and the volumes of the various layers can be within the ratio range of about 1:8 to about 8:1.

From a geometric standpoint, the various layers of the stacks described herein suitably have the same or a very similar facial surface area—that is the surface of the piezoelectric element layer and compliant layer that are adjacent suitably have a surface area that is within about 1%-20% of each other, such that they fit together and stack neatly. This allows for a maximum shared surface area contact, minimizing movement between the layers and improving the transfer of load between the layers. Suitably, the various layers of the stacks have both a similar thickness and a similar surface area, including dimeter (e.g., "d" in FIG. 1A) if a circular shaped layer is used. Though in other embodiments, the various layers can have varying thicknesses, suitably still within about 1%-20% of each other, while still maintaining a surface area that is within about 1%-20%. In other embodiments, the thicknesses can vary outside of this 1%-20% range, but still maintain a similar surface area. Suitably, the surface areas of the various layers is within about 1%-5% of each other, and more suitably are within a 1%-2% of each other, or less.

The piezoelectric element layers useful in the stacks described herein can include any suitable piezoelectric material, for example, lead zirconium titanate (PZT), barium titanate or polyvinylidene difluoride (PVDF). Other piezoelectric materials for use in the piezoelectric element layers described herein exhibit a Perovskite crystalline structure, i.e., the same type of crystal structure as calcium titanium oxide ($CaTiO_3$). In embodiments, suitable piezoelectric materials include but are not limited to, structures of hydroxyapatite, structures of apatite, structures of lithium sulfate monohydrate, structures of sodium potassium niobate, structures of quartz, structures of tartaric acid, aluminum nitride, bismuth titanate, gallium phosphate, lead scandium tantalite, lithium tantalate, etc. Other piezoelectric structures known in the art can also be used in the layers described herein.

The piezoelectric element layers 102 can also comprise a composite material, in which one or more piezoelectric materials, such as those described herein, are embedded or mixed within a polymeric matrix. Such structures can be polymeric matrixes that include one or more piezoelectric particles or piezoelectric fibers, contained within the polymeric matrix to create a composite. Such structures are disclosed in U.S. 2018/0296843, the disclosure of which is incorporated by reference herein in its entirety, particularly for the disclosure of the polymeric composite structures containing piezoelectric structures.

One or more of piezoelectric element layers 102 can also include a cofired stack consisting of single piezoelectric monolayers, or in other embodiments or groupings of piezoelectric monolayers, together to form piezoelectric element layer 102. Suitably, the piezoelectric monolayers are electrically connected to create the piezoelectric element layer.

In further embodiments, one or more of piezoelectric element layers 102 comprises a monolithic layer of piezoelectric material. In such embodiments, a single layer of a piezoelectric material is used in each of the piezoelectric element layers.

In still further embodiments, the types of piezoelectric element layers 102 can be mixed within the same stack such that the piezoelectric element layers alternate, or are randomly arranged, in the stack. In still further embodiments, the same type of structure is used for each of the piezoelectric element layers.

Exemplary polymers that can be used in preparing compliant layer 104, include for example, an epoxy, a polyethylene, or a polyether ether ketone (PEEK). Other suitable polymers can also be used. In exemplary embodiments, compliant layer 104 has a bulk modulus that is at least 30% less than a bulk modulus of any of the piezoelectric element layers of the stack. More suitably, each compliant layer 104 has a bulk modulus that is at least 50% less than a bulk modulus of each of the piezoelectric element layers of the stack. As used herein, the term "bulk modulus" refers to a measure of how resistant to compression the layers are, and is measured as the ratio of the infinitesimal pressure increase to the resulting relative decrease of the volume. Suitably, each compliant layer 104 has a bulk modulus that is at least 40% less than a bulk modulus of each of the piezoelectric element layers of the stack, more suitably at least 50% less, at least 60% less, at least 70% less, at least 80% less, or at least 90% less than a bulk modulus of each of the piezoelectric element layers of the stack.

In further embodiments, as shown in FIG. 1B, stacked piezoelectric energy harvester 100 can be encapsulated in an encapsulant 110. As used herein "encapsulant" includes a thin layer or application surrounding the stacked piezoelectric energy harvester, as well as thicker layers that can provide structural integrity to the stack. The thickness of the encapsulant can be on the order of microns or millimeters, up to centimeters, and even 10's to 100's of centimeters. Suitably the encapsulating coating is electrically insulating, such that the composite is electrically isolated (without the use of a wire or other connection) from the surroundings.

In embodiments, encapsulant 110 is a polymeric material, including for example an epoxy, a polyethylene, or a polyether ether ketone (PEEK). FIG. 1B also shows a traditional piezoelectric stack 112, which does not contain compliant layers 104 between adjacent piezoelectric element layers 102, but instead simply includes a minimum amount of adhesive, if any, between the layers prior to being encapsulated in encapsulant 110.

As described herein, it has been surprisingly determined that by utilizing compliant layers between piezoelectric element layers of a piezoelectric energy harvester, the power production of the energy harvester can be increased. It has been determined that if piezoelectric element layers are interspersed with compliant layers, suitably compliant layers having a similar surface area of contact (i.e., the surface area shared between adjacent piezoelectric element layers), but with thicknesses on the order of 0.2 mm or larger, the compliant layers can increase the power output of the energy harvester. Suitably, the thickness (i.e., $t_{104}$ in FIG. 1A) of the compliant layers is 0.2 mm or larger, 0.4 mm or larger, 0.8 mm or larger, 1 mm or larger, 2 mm or larger, 3 mm or larger, 4 mm or larger, 5 mm or larger, 6 mm or larger, 7 mm or larger, 10 mm or larger, etc., or about 0.2 mm to about 8 mm, about 0.2 mm to about 7 mm, about 0.2 mm to about 6 mm, about 0.2 mm to about 5 mm, about 0.2 mm to about 4 mm, about 0.2 mm to about 3 mm, about 0.2 mm to about 2 mm, about 0.2 mm to about 1 mm, about 0.2 mm to about 0.8 mm, about 0.2 mm to about 0.6 mm, about 0.4 mm to about 0.8 mm, or about 0.4 mm, about 0.6 m, about 0.8 mm or about 1 mm.

Use of only an adhesive layer (e.g., a thickness of about 5-10 micrometers (<0.01 mm)), for gluing adjacent stacked piezoelectric element layers together, did not produce these surprising and unexpected results (described herein with reference to a 0 mm compliant layer thickness. While increases in the thickness of an adhesive layer up to about 10 microns can improve the lifetime performance of the piezoelectric stacks, an increase in the energy conversion efficiency of the stacks is not found until the compliant layers described herein are utilized. As described herein, the inclusion of compliant layers between piezoelectric elements increases stress on the piezoelectric element, thus increasing power generation from the piezoelectric material, enhancing the ability to transform mechanical load into electric charge.

As described herein and as illustrated in FIGS. 1A, 2A and 2B, stacked piezoelectric energy harvester 100 suitably further includes one or more additional piezoelectric element layers 102'-102" and one or more additional compliant layers 104'-104'". As will be well understood, the number of piezoelectric element layers and compliant layers can be increased beyond that shown in the Figures, which are provided for illustrative purposes.

In embodiments, compliant layers (e.g., 104-104'") suitably each have the same thickness, though in other embodiments the thickness of each of the compliant layers can vary throughout the stack. In general however, each of the compliant layers within a stacked piezoelectric energy harvester has a thickness that is within about 50% of each other. That is the thickness of each compliant layer varies within about 50% (i.e., ±50% thickness variation from layer to layer) of all of the other compliant layers. More suitably, the compliant layers will have a thickness that is within about 40% of each other, or within about 30% of each other, or within about 20% of each other, or within about 10% of each other, or within about 5% of each other, or within about 1% of each other.

In further embodiments, piezoelectric element layers (e.g., 102-102") suitably each have the same thickness, though in other embodiments the thickness of each of the piezoelectric element layers can vary throughout the stack. In general however, each of the piezoelectric element layers within a stacked piezoelectric energy harvester has a thickness that is within about 50% of each other. That is the thickness of each piezoelectric element layer varies within about 50% (i.e., ±50% thickness variation from layer to layer) of all of the other piezoelectric element layers. More suitably, the piezoelectric element layers will have a thickness that is within about 40% of each other, or within about 30% of each other, or within about 20% of each other, or within about 10% of each other, or within about 5% of each other, or within about 1% of each other.

In additional embodiments, compliant layers (e.g., 104-104''') suitably each have the same volume, though in other embodiments the volume of each of the compliant layers can vary throughout the stack. In general however, each of the compliant layers within a stacked piezoelectric energy harvester has a volume that is within about 50% of each other. That is the volume of each compliant layer varies within about 50% (i.e., ±50% volume variation from layer to layer) of all of the other compliant layers. More suitably, the compliant layers will have a volume that is within about 40% of each other, or within about 30% of each other, or within about 20% of each other, or within about 10% of each other, or within about 5% of each other, or within about 1% of each other.

In further embodiments, piezoelectric element layers (e.g., 102-102") suitably each have the same volume, though in other embodiments the volume of each of the piezoelectric element layers can vary throughout the stack. In general however, each of the piezoelectric element layers within a stacked piezoelectric energy harvester has a volume that is within about 50% of each other. That is the volume of each piezoelectric element layer varies within about 50% (i.e., ±50% volume variation from layer to layer) of all of the other piezoelectric element layers. More suitably, the piezoelectric element layers will have a volume that is within about 40% of each other, or within about 30% of each other, or within about 20% of each other, or within about 10% of each other, or within about 5% of each other, or within about 1% of each other.

In additional embodiments, provided herein is a stacked piezoelectric energy harvester, comprising alternating layers of: N compliant layers; and N−1 piezoelectric element layers. For example, as shown in FIGS. 2A and 2B, N compliant layers, e.g., 104-104'''', and N−1 piezoelectric element layers, e.g., 102-102''', are adjacent one another, such that they are in contact with one another on a larger surface area side of the layer (i.e., not in contact on the thickness side of the layers).

In other embodiments, provided herein is a stacked piezoelectric energy harvester, comprising: alternating layers of: N−1 compliant layers; and N piezoelectric element layers.

N represents a whole integer between 3 and 100, suitably between 3 and 50, between 3 and 40, between 3 and 30, between 3 and 20, including 3, 4, 5, 6, 7, 8, 9, 10, 11, 12, 13, 14, 15, 16, 17, 18, 19 and 20. This, in embodiments, the number of piezoelectric layers is always one less than the number of compliant layers, such that the ends of a stack are each compliant layers. In other embodiments, the ends of the stack are piezoelectric element layers, such as in FIG. 2A (102 and 102"). In such embodiments, the piezoelectric energy harvester is suitably encapsulated in an encapsulant 110, as in FIG. 2B, resulting in a polymeric structure surrounding the stack, thereby providing a compliant structure at both ends of the stack.

As described herein, suitably a ratio of a volume of at least one of the piezoelectric element layers, to a volume of at least one of the compliant layers, is between about 1:8 to about 8:1 (volume piezoelectric:volume compliant), or a ratio of a thickness of at least one of the piezoelectric element layers, to a thickness of at least one of the compliant layers is between about 1:8 to about 8:1 (thickness piezoelectric:thickness compliant). In embodiments, both the ratios of the volumes and thicknesses can be between about 1:8 to about 8:1.

As shown in FIGS. 2A and 2B, the piezoelectric element layers of a stacked piezoelectric energy harvester are suitably electrically connected to each other. This electrical connection can include electrical connection of each of the individual piezoelectric element layers, suitably using a positive electrode 202 and a negative electrode 204. This electrical connection can take the form shown in FIG. 2A or 2B, where the piezoelectric element layers are electrically connected in parallel (while spatially arranged in series). In other embodiments, the piezoelectric element layers can be electrically connected in series. In still further embodiments, each of the separate piezoelectric element layers can be separately electrically connected to a desired output for the power generated by the stacked piezoelectric energy harvester.

As described herein, it has been surprisingly determined that the addition of the compliant layers to the piezoelectric energy harvesters described herein results in an increase in power production from the energy harvester. This increase in power production is suitably on the order of at least about 5% as compared to a stacked piezoelectric energy harvester without the compliant layer(s), i.e., where only a thin layer of adhesive or glue, if any, is used between adjacent piezoelectric elements in a stack. In suitable embodiments, the power production is increased by at least about 10% as compared to a stacked piezoelectric energy harvester without a compliant layer (or layers), more suitably the increase is at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100%.

Various mechanisms may be the reason behind the increase in power production, including electrical interactions. FIGS. 3A-3D illustrate an exemplary mechanism for the enhanced power production. Not wishing to be bound by theory, it is hypothesized that if a compliant layer is used between piezoelectric element layers, but is not constrained (e.g., FIGS. 3A and 3B), the compliant layer expands beyond the edges of the stack, and the increase in energy is not transferred to the energy harvester. However, if the compliant layers are constrained, such as in FIG. 3C, either via choice of compliant layer material or shape, or through an external mechanism constraining the expansion of the layers during loading, including for example an encapsulant, additional forces are created in the piezoelectric element due to the modulus differences between the layers, resulting in an increase in power produced. FIG. 3D shows a possible distribution of the shear stresses applied in the form of surface traction to the piezoelectric element. It can be seen that the shear strain, $\gamma(x,0)$ on the surface varies from zero to a maximum level at the end of the element as shown.

As described herein, the piezoelectric element layers can be a cofired stack consisting of single piezoelectric monolayers, suitably electrically connected. In other embodiments, the piezoelectric element layers can be groupings of piezoelectric monolayers 402, such as illustrated in FIGS. 4A and 4B. As shown, groupings of piezoelectric monolayers 402 can be surrounded, as well as separated by compliant layers 104, resulting in a stacked configuration. FIG. 4A shows a top view of an exemplary stack having a circular cross-section, though other shapes and orientations can be utilized. FIG. 4B shows a section through line B-B of the configuration in FIG. 4A, illustrating the groupings of piezoelectric monolayers 402. An encapsulant 110 can also be added to the stacked configuration, as described herein.

The piezoelectric element layers used in the various stacked piezoelectric energy harvesters described herein can be polarized or poled in various directions (polarized and poled are used interchangeably herein). Exemplary directions include the radial direction (i.e., the surface area-plane direction of the piezoelectric element layer) 502 as in FIG. 5A, the through-thickness direction (i.e., in the thickness plane of the piezoelectric element layer 504), or a shear direction (i.e. in the tangential plane of the piezoelectric element layer). To polarize the piezoelectric material (orient the dipoles in the desired direction—typically aligned with direction of applied force), a strong electric field (typically several kV/mm) is applied in the intended direction for a sufficient amount of time. When the electric field is removed, most of the dipoles remain aligned in the desired orientation. See, e.g., Jafee et al., Piezoelectric Ceramics, Academic Press, New York (1971) Chapters 1 and 11, the disclosures of which are incorporated by reference herein in their entireties. See also, Kiran et al., "Poling direction driven large enhancement in piezoelectric performance," *Scripta Materialia* 151:76-81 (2018), the disclosure of which is incorporated by reference herein in its entirety.

The piezoelectric element layers can each be polarized or poled in the same direction, in different directions, in alternating directions, etc. For example, as shown in FIG. 5A, the layers CAN alternate between radial 502 and through-thickness 504 poling. The direction of each radial or through-thickness poling can also be changed or alternated. In FIG. 5B, each of the piezoelectric layers is poled in a radial direction 502, with alternating radial coordinates (i.e., left and right). In FIG. 5C, each of the piezoelectric element layers is poled in a through-thickness direction 504, with alternating through-thickness coordinates (i.e., up and down). Other combinations and variations of poling directions and numbers of each layer that are poled in each direction can be varied. Suitably, a first piezoelectric element layer of a stack is poled in a first direction and a second piezoelectric element layer is poled in a second direction different from the first direction. In embodiments, a first piezoelectric element layer is poled in the radial direction and a second piezoelectric element layer is poled in the through-thickness direction. In other embodiments, both the first and second piezoelectric element layers can be poled in a radial direction 502, but with alternating radial coordinates, or both the first and second piezoelectric element layers can be poled in a through-thickness direction 504, but with alternating through-thickness coordinates.

The stacked piezoelectric energy harvesters described herein suitably collect and deliver energy to energy storage devices. Exemplary energy storage devices include various batteries, capacitors, etc. The stacked piezoelectric energy harvesters can also provide power in various scenarios and environments. In exemplary embodiments, the stacked piezoelectric energy harvesters include an electrode or other output to connect to an external device or system to which power can be provided.

For example, the stacked piezoelectric energy harvesters described herein can form components of various structures such as the following, where power can be provided. Exemplary structures and uses include power for pacemakers; power for implantable devices/sensors; load bearing parts to stimulate internal organ/tissue healing; lab on a chip devices that need power supplies; telemetry powering for sensing—"built in sensors"; tires on any vehicle to power rechargeable batteries and provide vibrational damping; drive shaft on a car to power rechargeable batteries; part of a car grill to power rechargeable batteries; surface on a floor to capture loads and convert to power; load-bearing structures in vibration generating devices in a household to feed to power grid; roads and bridges to capture vehicular loads; wind mills—blades or other structures loaded to generate power; plates/structures in oceans/seas to capture wave loads; bleachers in sport stadiums to power novelty lights or feed power into the grid as a function of fan loading of bleachers; body of cell phone to recharge batteries; structured components in building for energy harvest/sensors/damping; shingles on houses to translate wind forces and feed to power grid; bridge components for sensing/power generation; parts in power tools like jackhammers or drills for energy harvest/sensors/damping; parts of construction equipment for energy harvest/sensors/damping; mechanical damping with piezoelectric structures; use in structures in regions of high seismic activity to capture early detection and damping; hook up to grid to form a giant network of sensors; snow ski vibration damping and power production; self-heating boots; shoes with lighting; sensors for clothing; fabric made for various applications; sound proofing materials for damping; sails of sail boats to generate ship power; incorporate with any power plant system to increase efficiency; poles in power lines; piezoelectric transmission lines or conductive cables; road sensing lines/pads to trigger stop lights, sense presence of cars, etc.; self-powered exoskeleton; remote sensor with sustained power from loading/vibration; front fork on bike to power bike devices or provide vibration damping;

In exemplary embodiments, the stacked piezoelectric energy harvester is part of a tissue-stimulating implant, for example a spinal implant. In such embodiments, the stacked piezoelectric energy harvester can act as a power generator. For example, the stacked piezoelectric energy harvester can provide energy generation in the form of an alternating current (AC), which is conditioned with various signal conditioning circuits, and then output as a direct current (DC) via a tissue stimulating electrode.

As used herein, a "tissue-stimulating implant" as described throughout is an implant introduced into a patient (including animals or humans) so as to provide electric stimulation to a tissue of a patient when the stacked piezoelectric energy harvester is placed under mechanical loads. Exemplary tissues include, but are not limited to, bone, muscle, nerves, cartilage, tendons and organs (e.g., brain, heart, lungs). Electric stimulation may also be provided to cells within the body. Suitably, the patients are mammals, including humans, dogs, cats, mice, rats, monkeys, etc.

In embodiments, the tissue-stimulating implants are bone-stimulating implants, and in exemplary embodiments are spinal implants for spinal fusion. The electric stimulation produced by the implants in stimulation of bone growth and osseointegration of the encapsulated composite. Other bone-stimulating implants can also be prepared using dimensions and orientations know in the art as necessitated by the positioning in the body.

Exemplary tissue-stimulating implants that can be produced according to the methods provided herein include bone plates, bone screws, bone implants, spinal implants, etc.

In embodiments, the tissue-stimulating implants described herein are strain coupled to bone or other body tissue so as to generate charge as the tissue undergoes strain, and the generated charge is applied via electrodes to a region where it is desired to stimulate a tissue, e.g., bone growth (see, e.g., U.S. Pat. No. 6,143,035, the entire disclosure of which is incorporated by reference herein in its entirety for all purposes). In embodiments, the implants described herein can be attached by pins or bone screws to a bone and the poles of the piezoelectric element are connected via leads to carry the charge remotely and couple the charge to promote healing.

In further embodiments, provided herein is a method of increasing the power production of a stacked piezoelectric energy harvester having two or more piezoelectric element layers. The method includes layering a compliant layer between each piezoelectric element layer of the energy harvester. As described herein, a ration of a volume of at least one of the piezoelectric element layers, to a volume of at least one of the compliant layers is between about 1:8 to about 8:1 (volume piezoelectric:volume compliant), or a ratio of a thickness of at least one of the piezoelectric element layers, to a thickness of at least one of the compliant layers is between about 1:8 to about 8:1 (thickness piezoelectric:thickness compliant).

As described throughout, it has been surprisingly found that the inclusion of a compliant layer between piezoelectric element layers in a stack configuration greatly increases the power production of the stacked piezoelectric energy harvester, suitably on the order of at least 10%, more suitably at least 30%, compared to stacked piezoelectric energy harvesters without compliant layers.

Suitable materials and structures for the piezoelectric element layers and compliant layers are described herein, along with exemplary geometric proportions, shapes, etc.

As described herein, in exemplary embodiments, the methods of increasing the power production of a stacked piezoelectric energy harvester further include poling the piezoelectric element layers. Exemplary directions for the poling include the radial direction, a shear direction, or a through-thickness direction. Suitably the method includes poling at least one piezoelectric element layer in a first direction and at least one piezoelectric element layer in a second direction different from the first direction.

Also provided herein are methods of providing power generation from the stacked piezoelectric energy harvester as described herein, comprising loading the stacked piezoelectric energy harvester with a load of at least about 100 N.

In exemplary embodiments the stacked piezoelectric energy harvester is loaded with a load of at least about 200 N, at least about 300 N, at least about 400 N, at least about 500 N, at least about 600 N, at least about 700 N, at least about 800 N, at least about 900 N, at least about 1000 N, at least about 1100 N, at least about 1200 N, at least about 1300 N, at least about 1400 N, at least about 1500 N, or at least about 2000 N.

The frequency of the load applied to the piezoelectric energy harvester is generally on the order of about 0.5 to about 100 Hz, more suitably about 1-50 Hz, or 1-5 Hz, or about 1-3 Hz. For example, a load of at least about 1000 N can be applied at a frequency of about 1-5 Hz.

The loading can be provided by various sources, including for example, by the motion of mammal, such as by the walking of a human or an animal, for example, to a stacked piezoelectric energy harvester that is part of a tissue stimulating implant of a patient, such as a spinal implant. The loading can also be provided by a motion of a machine or a vehicle, including a car or truck traveling over a road or bridge. Other loading mechanisms include various cyclic or non-cyclic loadings as described herein in various scenarios and environments where loading of a piezoelectric energy harvester can be utilized to provide power generation.

Embodiment 1 is a stacked piezoelectric energy harvester, comprising a first piezoelectric element layer; a first compliant layer positioned adjacent the first piezoelectric element layer; and a second piezoelectric element layer positioned adjacent the first compliant layer, wherein a ratio of a volume of the first piezoelectric element layer and/or a volume of the second piezoelectric element layer, to a volume of the first compliant layer is between about 1:8 to about 8:1 (volume piezoelectric:volume compliant), or wherein a ratio of a thickness of the first piezoelectric element layer and/or a thickness of the second piezoelectric element layer, to a thickness of the first compliant layer is between about 1:8 to about 8:1 (thickness piezoelectric:thickness compliant).

Embodiment 2 includes the stacked piezoelectric energy harvester of embodiment 1, wherein the first piezoelectric element layer comprises lead zirconium titanate, barium titanate or polyvinylidene difluoride (PVDF).

Embodiment 3 includes the stacked piezoelectric energy harvester of embodiment 1 or embodiment 2, wherein the first compliant layer comprises a polymer.

Embodiment 4 includes the stacked piezoelectric energy harvester of embodiment 3, wherein the polymer is an epoxy, a polyethylene, or a polyether ether ketone (PEEK).

Embodiment 5 includes the stacked piezoelectric energy harvester of any of embodiments 1-4, wherein the first compliant layer has a bulk modulus that is at least 50% less than a bulk modulus of the first piezoelectric element layer and/or the second piezoelectric element layer.

Embodiment 6 includes the stacked piezoelectric energy harvester of any of embodiments 1-5, further comprising a polymer encapsulating the stacked piezoelectric energy harvester.

Embodiment 7 includes the stacked piezoelectric energy harvester of any of embodiments 1-6, wherein the ratio of the volume of the first piezoelectric element layer and/or the volume of the second piezoelectric element layer, to the volume of the first compliant layer is between about 1:4 to about 1:8 (volume piezoelectric:volume compliant).

Embodiment 8 includes the stacked piezoelectric energy harvester of any of embodiments 1-6, wherein the ratio of the thickness of the first piezoelectric element layer and/or the thickness of the second piezoelectric element layer, to the thickness of the first compliant layer is between about 1:4 to about 1:8 (thickness piezoelectric:thickness compliant).

Embodiment 9 includes the stacked piezoelectric energy harvester of any of embodiments 1-8, wherein the first compliant layer has a thickness of about 0.2 mm to about 8 mm.

Embodiment 10 includes the stacked piezoelectric energy harvester of embodiment 9, wherein the first compliant layer has a thickness of about 0.4 mm to about 0.8 mm.

Embodiment 11 includes the stacked piezoelectric energy harvester of any of embodiments 1-8, further comprising one or more additional piezoelectric element layers and one or more additional compliant layers.

Embodiment 12 includes the stacked piezoelectric energy harvester of embodiment 11, wherein each of the compliant layers has a thickness within about 40% of each other.

Embodiment 13 includes the stacked piezoelectric energy harvester of embodiment 11, wherein each of the compliant layers has a thickness within about 10% of each other.

Embodiment 14 includes the stacked piezoelectric energy harvester of embodiment 11, wherein each of the piezoelectric element layers has a thickness within about 40% of each other.

Embodiment 15 includes the stacked piezoelectric energy harvester of embodiment 11, wherein each of the piezoelectric element layers has a thickness within about 10% of each other.

Embodiment 16 includes the stacked piezoelectric energy harvester of embodiment 11, wherein each of the compliant layers has a volume within about 40% of each other.

Embodiment 17 includes the stacked piezoelectric energy harvester of embodiment 11, wherein each of the compliant layers has a volume within about 10% of each other.

Embodiment 18 includes the stacked piezoelectric energy harvester of embodiment 11, wherein each of the piezoelectric element layers has a volume within about 40% of each other.

Embodiment 19 includes the stacked piezoelectric energy harvester of embodiment 11, wherein each of the piezoelectric element layers has a volume within about 10% of each other.

Embodiment 20 includes the stacked piezoelectric energy harvester of any of embodiments 1-19, wherein the stacked piezoelectric energy harvester provides an increase in power production of at least about 10% as compared to a stacked piezoelectric energy harvester without the first compliant layer.

Embodiment 21 includes the stacked piezoelectric energy harvester of any of embodiments 1-20, wherein each of the piezoelectric element layers is poled in a radial direction, a shear direction, or a through-thickness direction.

Embodiment 22 includes the stacked piezoelectric energy harvester of embodiment 21, wherein the first piezoelectric element layer is poled in a first direction and the second piezoelectric element layer is poled in a second direction different from the first direction.

Embodiment 23 includes the stacked piezoelectric energy harvester of embodiment 21, wherein the first piezoelectric element layer is poled in the radial direction and the second piezoelectric element layer is poled in the through-thickness direction.

Embodiment 24 includes the stacked piezoelectric energy harvester of any of embodiments 1-23, wherein the first and/or second piezoelectric element layer comprises a cofired stack consisting of single piezoelectric monolayers or groupings of piezoelectric monolayers.

Embodiment 25 includes the stacked piezoelectric energy harvester of embodiment 24, wherein the piezoelectric monolayers are electrically connected.

Embodiment 26 includes the stacked piezoelectric energy harvester of any of embodiments 1-23, wherein the first and/or second piezoelectric element layer comprises a monolithic layer of piezoelectric material.

Embodiment 27 includes the stacked piezoelectric energy harvester of any of embodiments 1-26 wherein the stacked piezoelectric energy harvester collects and delivers energy to an energy storage device.

Embodiment 28 includes the stacked piezoelectric energy harvester of any of embodiments 1-27, wherein the stacked piezoelectric energy harvester is part of a tissue-stimulating implant.

Embodiment 29 includes the stacked piezoelectric energy harvester of embodiment 28, wherein the tissue-stimulating implant is a spinal implant.

Embodiment 30 is a stacked piezoelectric energy harvester, comprising alternating layers of: N compliant layers; and N−1 piezoelectric element layers; wherein the compliant layers and the piezoelectric element layers are adjacent one another, wherein N is a whole integer between 3 and 20, and wherein a ratio of a volume of at least one of the piezoelectric element layers, to a volume of at least one of the compliant layers is between about 1:8 to about 8:1 (volume piezoelectric:volume compliant), or wherein a ratio of a thickness of at least one of the piezoelectric element layers, to a thickness of at least one of the compliant layers is between about 1:8 to about 8:1 (thickness piezoelectric:thickness compliant).

Embodiment 31 includes the stacked piezoelectric energy harvester of embodiment 30 wherein, the piezoelectric element layers are electrically connected to each other.

Embodiment 32 includes the stacked piezoelectric energy harvester of embodiment 30 or embodiment 31, wherein the piezoelectric element layers comprise lead zirconium titanate, barium titanate or polyvinylidene difluoride (PVDF).

Embodiment 33 includes the stacked piezoelectric energy harvester of any of embodiments 30-32, wherein the compliant layers comprise a polymer.

Embodiment 34 includes the stacked piezoelectric energy harvester of embodiment 33, wherein the polymer is an epoxy, a polyethylene, or a polyether ether ketone (PEEK).

Embodiment 35 includes the stacked piezoelectric energy harvester of any of embodiments 30-34, wherein each of the compliant layers has a bulk modulus that is at least 50% less than a bulk modulus of each of the piezoelectric element layers.

Embodiment 36 includes the stacked piezoelectric energy harvester of any of embodiments 30-35, further comprising a polymer encapsulating the stacked piezoelectric energy harvester.

Embodiment 37 includes the stacked piezoelectric energy harvester of any of embodiments 30-36, wherein the ratio of the volume of each of the piezoelectric element layers, to the volume of each of the compliant layers is between about 1:4 to about 1:8 (volume piezoelectric:volume compliant).

Embodiment 38 includes the stacked piezoelectric energy harvester of any of embodiments 30-36, wherein the ratio of the thickness of each of the piezoelectric element layers, to the thickness of each of the compliant layers is between about 1:4 to about 1:8 (thickness piezoelectric:thickness compliant).

Embodiment 39 includes the stacked piezoelectric energy harvester of any of embodiments 30-38, wherein each of the compliant layers has a thickness of about 0.2 mm to about 8 mm.

Embodiment 40 includes the stacked piezoelectric energy harvester of embodiment 39, wherein each of the compliant layers has a thickness of about 0.4 mm to about 0.8 mm.

Embodiment 41 includes the stacked piezoelectric energy harvester of any of embodiments 30-40, wherein each of the compliant layers has a thickness within about 40% of each other.

Embodiment 42 includes the stacked piezoelectric energy harvester of embodiment 41, wherein each of the compliant layers has a thickness within about 10% of each other.

Embodiment 43 includes the stacked piezoelectric energy harvester of any of embodiments 30-42, wherein each of the piezoelectric element layers has a thickness within about 40% of each other.

Embodiment 44 includes the stacked piezoelectric energy harvester of embodiment 43, wherein each of the piezoelectric element layers has a thickness within about 10% of each other.

Embodiment 45 includes the stacked piezoelectric energy harvester of any of embodiments 30-44, wherein N is 8.

Embodiment 46 includes the stacked piezoelectric energy harvester of any of embodiments 30-44, wherein N is 16.

Embodiment 47 includes the stacked piezoelectric energy harvester of any of embodiments 30-46, wherein the stacked piezoelectric energy harvester provides an increase in power production of at least about 10% as compared to a stacked piezoelectric energy harvester without the first compliant layer.

Embodiment 48 includes the stacked piezoelectric energy harvester of any of embodiments 30-47, wherein each of the piezoelectric element layers is poled in a radial direction, a shear direction, or a through-thickness direction.

Embodiment 49 includes the stacked piezoelectric energy harvester of embodiment 48, wherein at least one piezoelectric element layer is poled in a first direction and at least one piezoelectric element layer is poled in a second direction different from the first direction.

Embodiment 50 includes the stacked piezoelectric energy harvester of embodiment 48, wherein a polling of the piezoelectric element layers alternates between a radial direction and a through-thickness direction.

Embodiment 51 includes the stacked piezoelectric energy harvester of any of embodiments 30-50, wherein at least one of the piezoelectric element layers comprises a cofired stack consisting of single piezoelectric monolayers or groupings of piezoelectric monolayers.

Embodiment 52 includes the stacked piezoelectric energy harvester of embodiment 51, wherein the piezoelectric monolayers are electrically connected.

Embodiment 53 includes the stacked piezoelectric energy harvester of any of embodiments 30-52, wherein at least one of the piezoelectric element layers comprises a monolithic layer of piezoelectric material.

Embodiment 54 includes the stacked piezoelectric energy harvester of any of embodiments 30-53, wherein the stacked piezoelectric energy harvester collects and delivers energy to an energy storage device.

Embodiment 55 includes the stacked piezoelectric energy harvester of any of embodiments 30-54, wherein the stacked piezoelectric energy harvester is part of a tissue-stimulating implant.

Embodiment 56 includes the stacked piezoelectric energy harvester of embodiment 55, wherein the tissue-stimulating implant is a spinal implant.

Embodiment 57 is a method of increasing the power production of a stacked piezoelectric energy harvester having two or more piezoelectric element layers, comprising layering a compliant layer between each piezoelectric element layer of the energy harvester, wherein a ratio of a volume of at least one of the piezoelectric element layers, to a volume of at least one of the compliant layers is between about 1:8 to about 8:1 (volume piezoelectric:volume compliant), or wherein a ratio of a thickness of at least one of the piezoelectric element layers, to a thickness of at least one of the compliant layers is between about 1:8 to about 8:1 (thickness piezoelectric:thickness compliant).

Embodiment 58 includes the method of embodiment 57, wherein the piezoelectric element layers element layers comprise lead zirconium titanate, barium titanate or polyvinylidene difluoride (PVDF).

Embodiment 59 includes the method of embodiment 57 or embodiment 58, wherein compliant layers comprise a polymer.

Embodiment 60 includes the method of embodiment 59, wherein the polymer is an epoxy, a polyethylene, or a polyether ether ketone (PEEK).

Embodiment 61 includes the method of any one of embodiments 57-60, further comprising encapsulating the stacked piezoelectric energy harvester in a polymer.

Embodiment 62 includes the method of any one of embodiments 57-61, wherein the ratio of the volume of each of the piezoelectric element layers, to the volume of each of the compliant layers is between about 1:4 to about 1:8 (volume piezoelectric:volume compliant).

Embodiment 63 includes the method of any one of embodiments 57-61, wherein the ratio of the thickness of each of the piezoelectric element layers, to the thickness of each of the compliant layers is between about 1:4 to about 1:8 (thickness piezoelectric:thickness compliant).

Embodiment 64 includes the method of any one of embodiments 57-63, wherein each of the compliant layers has a thickness of about 0.2 mm to about 8 mm.

Embodiment 65 includes the method of embodiment 64, wherein each of the compliant layers has a thickness of about 0.4 mm to about 0.8 mm.

Embodiment 66 includes the method of any one of embodiments 57-65, wherein each of the compliant layers has a thickness within about 40% of each other.

Embodiment 67 includes the method of embodiment 66, wherein each of the compliant layers has a thickness within about 10% of each other.

Embodiment 68 includes the method of any one of embodiments 57-67, wherein each of the piezoelectric element layers has a thickness within about 40% of each other.

Embodiment 69 includes the method of embodiment 68, wherein each of the piezoelectric element layers has a thickness within about 10% of each other.

Embodiment 70 includes the method of any one of embodiments 57-69, wherein the power production is increased by at least about 10% as compared to a stacked piezoelectric energy harvester without the compliant layers.

Embodiment 71 includes the method of embodiment 70, wherein the power production is increased by at least about 30% as compared to the stacked piezoelectric energy harvester without the compliant layers.

Embodiment 72 includes the method of any one of embodiments 57-71, wherein each of the compliant layers has a bulk modulus that is at least 50% less than a bulk modulus of each of the piezoelectric element layers.

Embodiment 73 includes the method of any one of embodiments 57-72, further comprising poling at least one of the piezoelectric element layers in a radial direction, a shear direction, or a through-thickness direction.

Embodiment 74 includes the method of embodiment 73, wherein at least one piezoelectric element layer is poled in a first direction and at least one piezoelectric element layer is poled in a second direction different from the first direction.

Embodiment 75 includes the method of embodiment 74, wherein a polling of the piezoelectric element layers alternates between a radial direction and a through-thickness direction.

Embodiment 76 includes the method of any one of embodiments 57-75, wherein the stacked piezoelectric energy harvester is part of a tissue-stimulating implant.

Embodiment 77 includes the method of embodiment 76, wherein the tissue-stimulating implant is a spinal implant.

Embodiment 78 is a method of providing power generation from the stacked piezoelectric energy harvester of embodiment 1 or embodiment 30, comprising loading the stacked piezoelectric energy harvester with a load of at least about 100 N.

Embodiment 79 includes the method of embodiment 78, comprising loading the stacked piezoelectric energy harvester with the load of at least about 1000 N at a frequency of about 1-5 Hz.

Embodiment 80 includes the method of embodiment 79, wherein the loading is provided by a motion of a mammal.

Embodiment 81 includes the method of embodiment 79, wherein the loading is provided by a motion of a machine or a vehicle.

Embodiment 82 includes the method of embodiment 78, wherein the power generation is provided to a tissue-stimulating implant of a patient.

Embodiment 83 includes the method of embodiment 82, wherein the tissue-stimulating implant is a spinal implant.

EXAMPLES

Example 1: Effect of Compliant Layers in Piezoelectric Composite Energy Harvester for Spinal Fusion Applications In order to toughen the material for use in spinal fusion devices, the effect of adding a compliant layer between PZT discs on power generation was investigated in energy harvesting stacks for low impedance, low frequency human body motion.

Methods: Composite piezoelectric stacks were manufactured using four different compliant layer thicknesses between each PZT disc (n=5 in each group). For each stack, five pre-poled and electroded discs (10 mm×0.4 mm, STEMiNC) were connected electrically in parallel (EPO-TEK® H20E), and stacked mechanically in series. Slices of cured epoxy (EPO-TEK® 301) of varying thicknesses (0, 0.2, 0.4, and 0.8 mm±0.02 mm) were adhered between each disc. The stacks were encapsulated with medical grade epoxy (EPO-TEK® 301) keeping the volume of PZT, overall height, and surface area constant. Using an MTS Mini-Bionix 858 with self-aligning platen, each stack was electromechanically tested. To simulate physiological loading in the lumbar spine, a 1200N preload was applied, followed by cyclic compression at three loads (100, 500, 1000N) and 2 Hz. Voltage was measured across a range of resistances (0.015 MΩ-63.4 MΩ) and power generated was calculated for each test condition. A two-way ANOVA was used to compare power production as a function of compliant layer thickness and resistance for each load ($\alpha < 0.05$).

Figure 6:
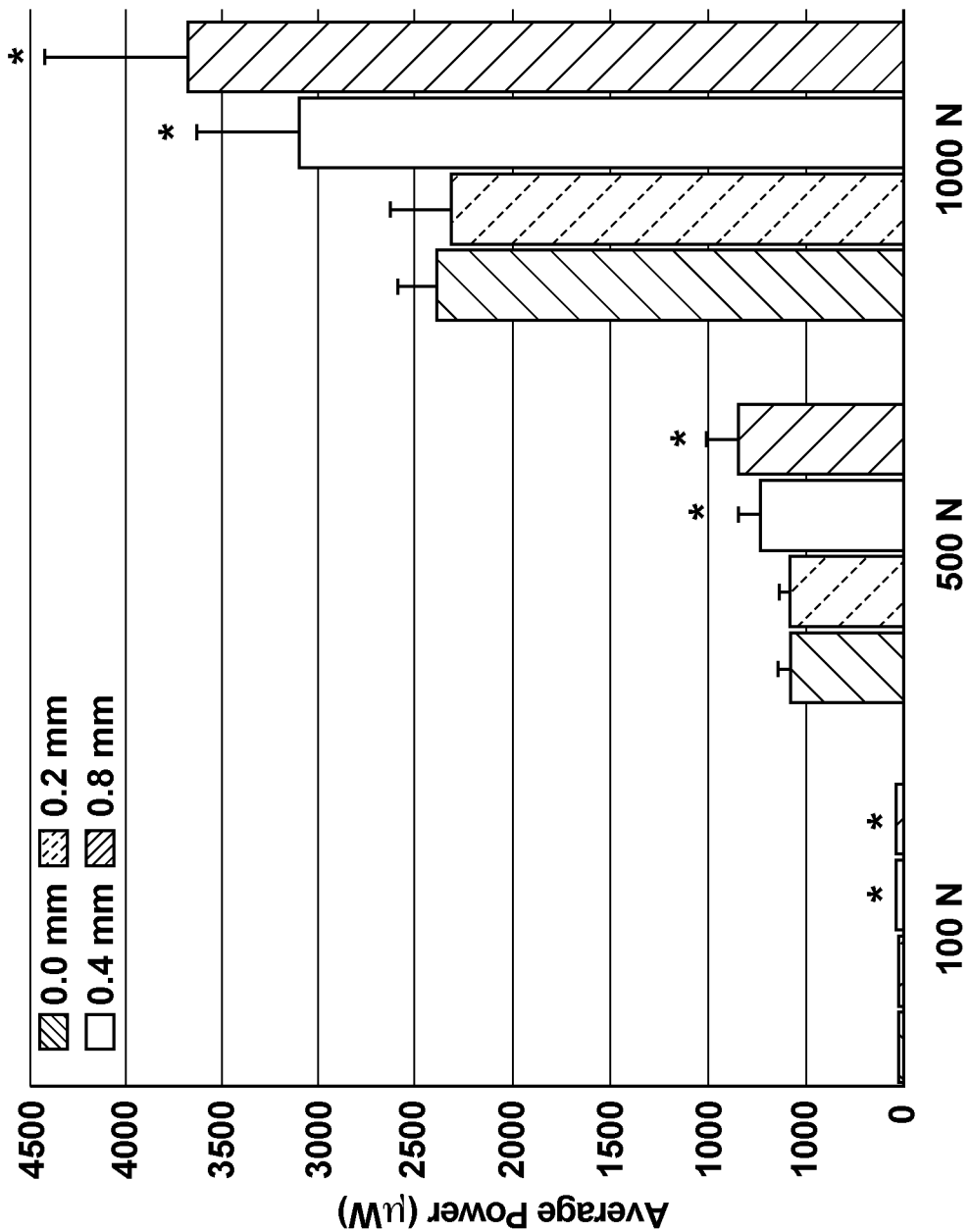
FIG. 6 shows average power as a function of compliant layer thickness and mechanical loading at 6 MΩ. * represents significant difference from the 0 mm group (p<0.05).
Figure 7:
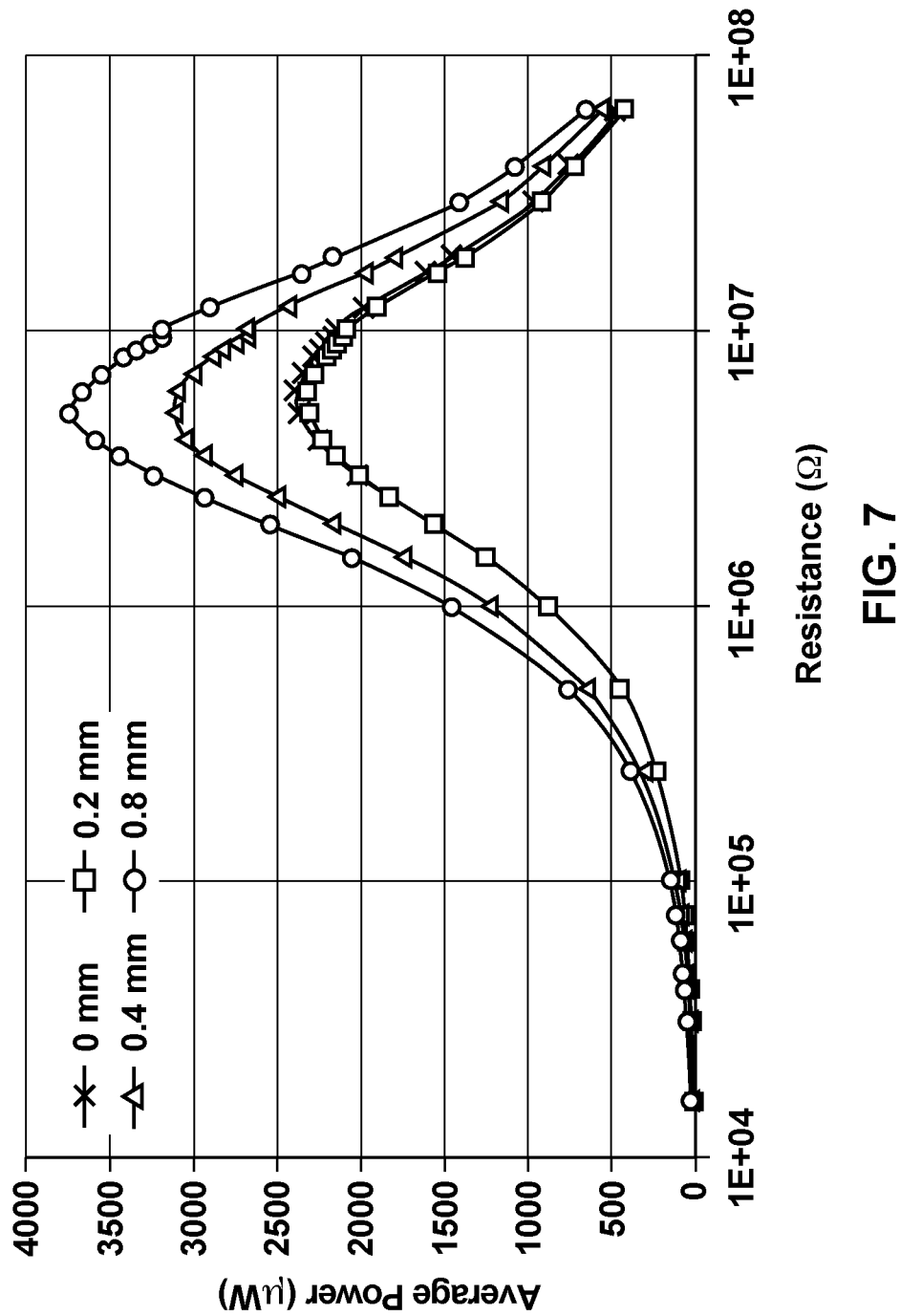
FIG. 7 shows power output as a function of compliant layer thickness and resistance load at 1000 N and 2 Hz.

Results: The average power generated for each stack type as a function of load and compliant layer thickness is shown in FIG. 6. Increased mechanical load levels significantly increased power output for all groups ($p < 0.05$). There was no statistical difference between the 0 mm and 0.2 mm groups for all loads across the resistance sweep. Additionally, both the 0.4 mm and 0.8 mm stacks produced significantly more power as compared to the 0 mm, but were not statistically different from each other. At maximum power, there were 0, 1.2, and 1.7 fold increases between the 0 mm group and the 0.2, 0.4, and 0.8 mm groups respectively (FIG. 7). This trend held true across the resistance sweep ($p < 0.05$). Similarly, the change in thickness of the compliant layer did not affect the resistance at which maximum power occurred for all groups.

Conclusions: The addition of a compliant layer significantly increased the power produced by the stacks across all mechanical loading conditions and resistances while PZT volume remained constant. Utilizing a PZT composite disc stack lowered the source impedance at maximum power output, while maintaining the tough mechanical properties, both important in spinal implant materials.

Figure 8:
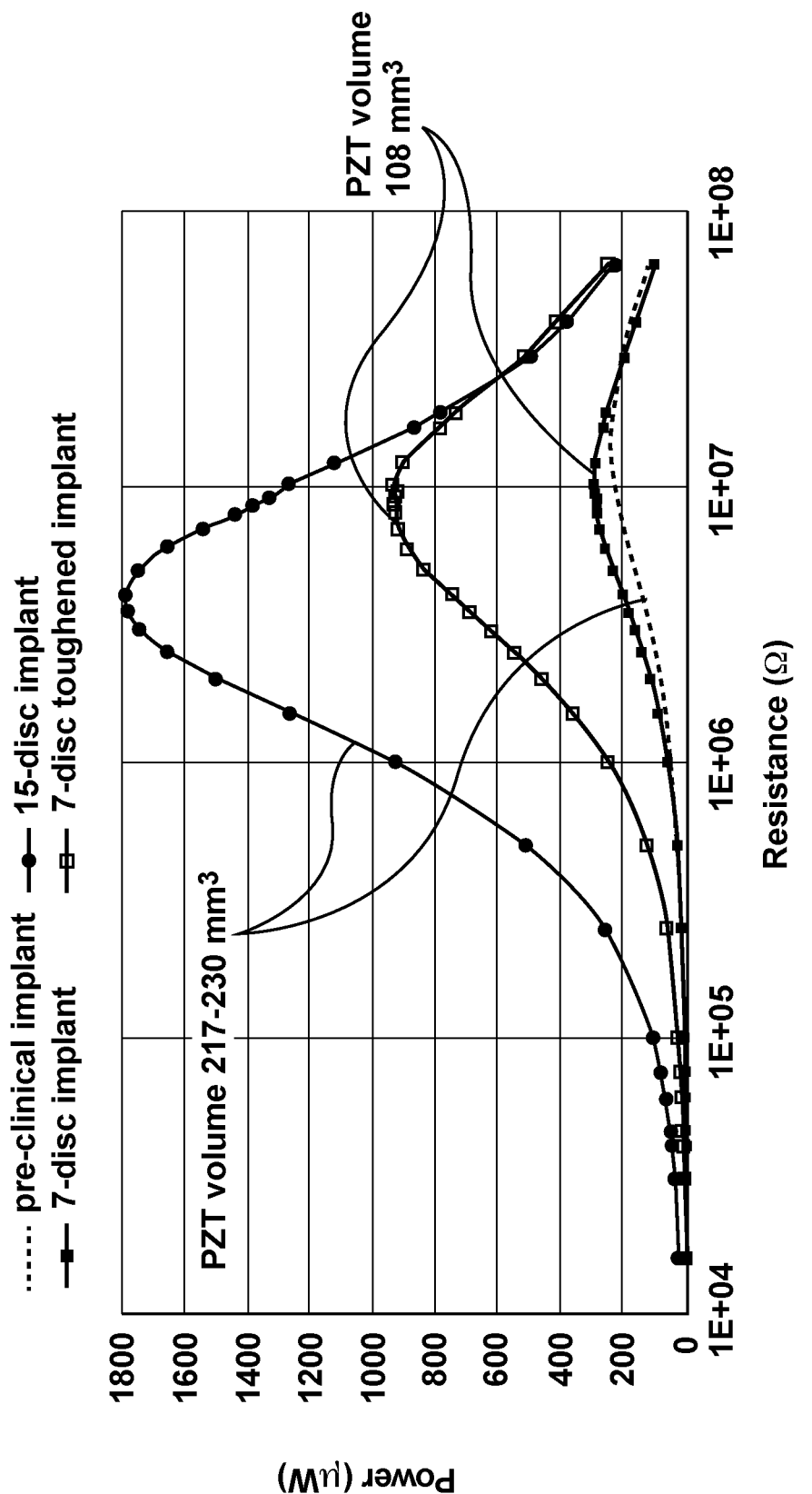
FIG. 8 shows power characterization of PZT/compliant layer implants compared to a pre-clinical fiber composite implant. Implants with matching PZT volumes are indicated.

Example 2: Using Stacked PZT Discs to Generate Power for DC Stimulation in a Composite Spinal Fusion Implant This Example evaluates the electromechanical properties of three composite PZT insert configurations that reduce manufacturing limitations within a spinal interbody and validate their use as a generator for DC stimulation.
Methods Three configurations of piezoelectric inserts (n=4) were made using pre-poled and electroded 7×0.4 mm PZT-4 discs connected electrically in parallel while stacked mechanically in series. Inserts were designed to fit within a 17×10× 23 mm custom transforaminal lumbar interbody fusion (TLIF) implant. The three configurations were: 15-disc, 7-disc, and 7-disc toughened with a 0.4 mm compliant layer of epoxy between each disc. Medical-grade epoxy was used to encapsulate each insert to the final implant shape. Once cured, each implant was loaded at 1000N peak-to-peak at 2 Hz for 15 cycles under a 1200N pre-load representing physiological lumbar loading. The voltage produced was measured across resistive loads from 984Ω to 63.4 MΩ. Power was calculated from measured voltages using Joule's Law and compared between the three insert configurations as well as a pre-clinical fiber implant, using a two-way ANOVA with a Tukey-Kramer post-hoc test ($\alpha = 0.05$).
Results The 15-disc implant and the pre-clinical fiber implant had PZT volumes of 217 mm$^3$ and 230 mm$^3$ respectively. Discs were significantly more efficient at producing power across the resistance sweep compared to fibers given similar volumes of PZT ($p < 0.01$). Both 7-disc implants had PZT volumes of 108 mm$^3$. Given identical volumes of PZT, toughened implants that included the compliant layers were able to produce significantly more power across the resistance sweep ($p < 0.01$). The two-way ANOVA resulted in a significant interaction between implant type and applied resistance ($p < 0.01$) (FIG. 8).

Discussion

To validate the switch from PZT fibers to discs, power output was compared for similar volumes of PZT. Discs produced more power than fibers, making them a desirable material for use in a composite spinal implant. Additionally, the compliant layers between stacks of PZT discs allowed for more power generated per unit volume of PZT due to increased strain experienced by each disc. This study established PZT discs as a viable power source needed to provide DC stimulation for bone growth in a spinal fusion interbody.

Example 3: Compliant Layer Adaptive Composite Stacks (CLACS) for Power Generation Providing DC Stimulation in Low Frequency Applications To increase efficiency of power generation at low frequencies, the effect of compliant layers between piezoelectric discs was investigated.

Methods

Compliant Layer Adaptive Composite Stacks (CLACS) were manufactured using 5 pre-poled and electroded PZT discs (10 mm×0.4 mm, STEMiNC). Discs were connected electrically in parallel and stacked mechanically in series with a layer of cured epoxy of varying thickness adhered between each disc (0.0, 0.2, 0.4, 0.8±0.02 mm). Stacks were encapsulated in medical grade epoxy (EPO-TEK® 301), keeping PZT volume, overall surface area and height constant. Each stack was electromechanically tested using a 1200 N preload and 1000 N cyclic load at four frequencies (1 Hz, 2 Hz, 3 Hz, and 5 Hz). Voltage was measured across a resistance sweep (984Ω-63.4 MΩ) for each loading condition. Power as a function of compliant layer thickness was compared for each frequency (two-way ANOVA, Tukey-Kramer, $\alpha=0.05$).

Results

Figure 9:
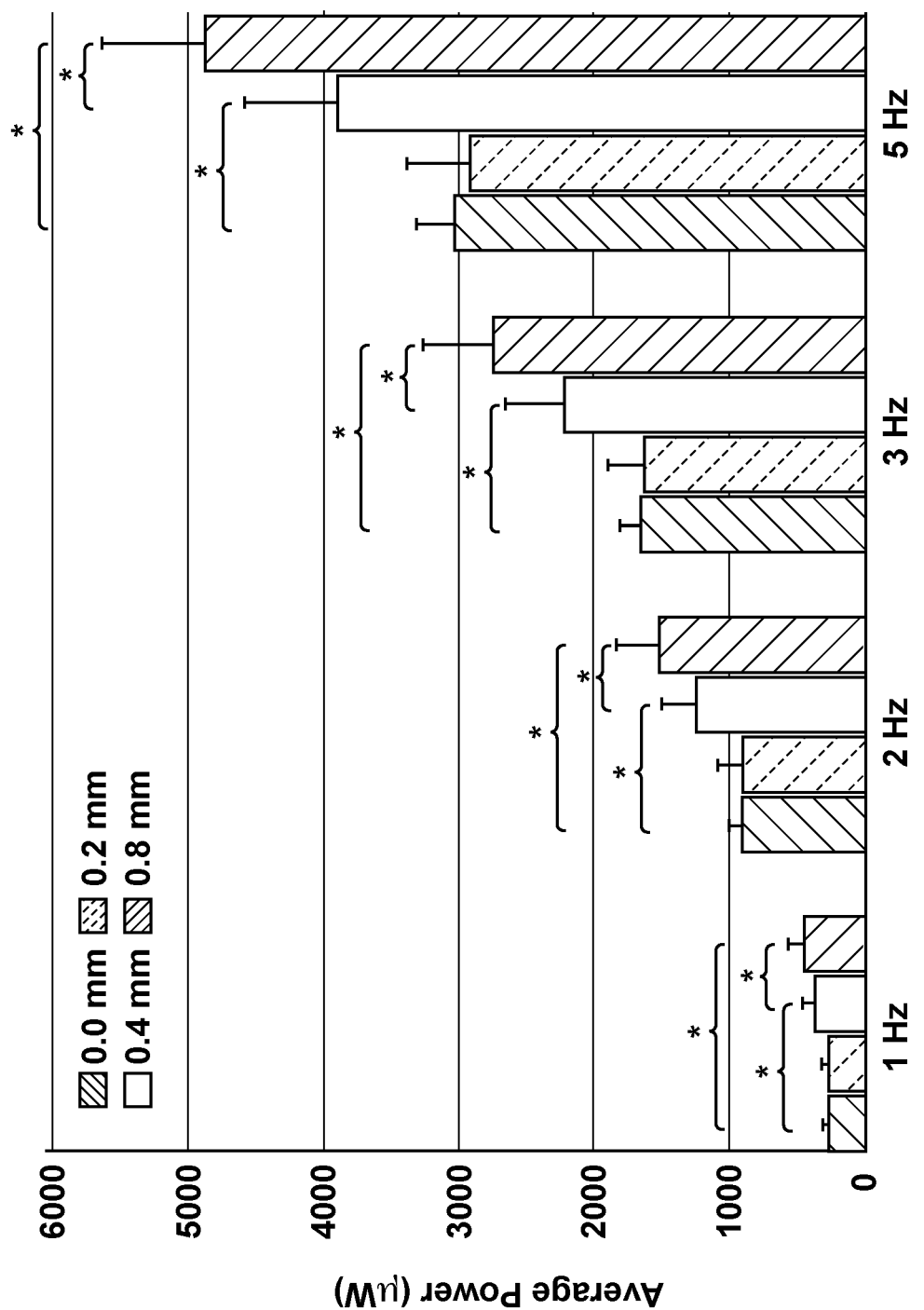
FIG. 9 shows average power as a function of compliant layer thickness and frequency at 2.5 MΩ. * represents significant difference (p<0.05).

There were 0, 1.2, and 1.7 fold increases in maximum power generated between the 0.0 mm group and the 0.2, 0.4, and 0.8 mm groups respectively. This trend held true across the resistance sweep and at each frequency, with no statistical difference between the 0.0 mm and 0.2 mm groups. There was significant difference between the other groups, as seen in FIG. 9 ($p<0.01$). Increasing frequency significantly increased power output for all groups ($p<0.05$). Frequency changes had a larger effect on power output with increasing compliant layer thickness.

Discussion

The addition of a compliant layer in the CLACS increases strain in the PZT, thus producing more power. The use of CLACS for power generation under low frequencies provides an effective method to provide DC stimulation to improve bone growth without the use of a battery in multiple orthopedic devices.

Example 4: Ultrasound Stimulation of Piezoelectric Composite Harvester with Compliant Layers for Bone Healing For patients with limited weight bearing abilities, a method of mechanically stimulating a piezoelectric material through ultrasound is beneficial. As described herein, compliant layers are inserted between stacked discs of PZT. This example investigates the energy generation potential of piezoelectric composites using medical imaging ultrasound as the loading source.

Methods: Medical imaging ultrasound was used to mechanically load piezoelectric composites through various media and distances perpendicular to the disc face. An Acuson 128×p Ultrasound Imaging Machine with a V4 probe (4 MHz vector array—128 PZT elements) and a Tektronix DPO 3034 Digital Phosphor Oscilloscope (300 MHz sampling rate) were used as the sound source system and measurement device respectively. Six pre-poled PZT discs (10 mm×0.4 mm, STEMiNC) were connected electrically in parallel (EPO-TEK® H20E), and stacked mechanically in series. Slices of cured epoxy (EPO-TEK® 301) of varying compliant layer thicknesses (0, 0.2, 0.4, and 0.8 mm±0.02 mm) were adhered between discs for mechanical stacking. The specimens were tested in three media, including tap water, muscle tissue, and muscle plus bone. Ultrasound signals were loaded in the perpendicular direction, and two distances, 20 mm and 40 mm, between the ultrasound probe and specimen were tested. The electrical signal (AC) output from each specimen was recorded off the oscilloscope and then analyzed using MATLAB to calculate peak voltage values and a two-way ANOVA ($\alpha=0.05$) was used to assess differences for each combination tested.

Figure 10:
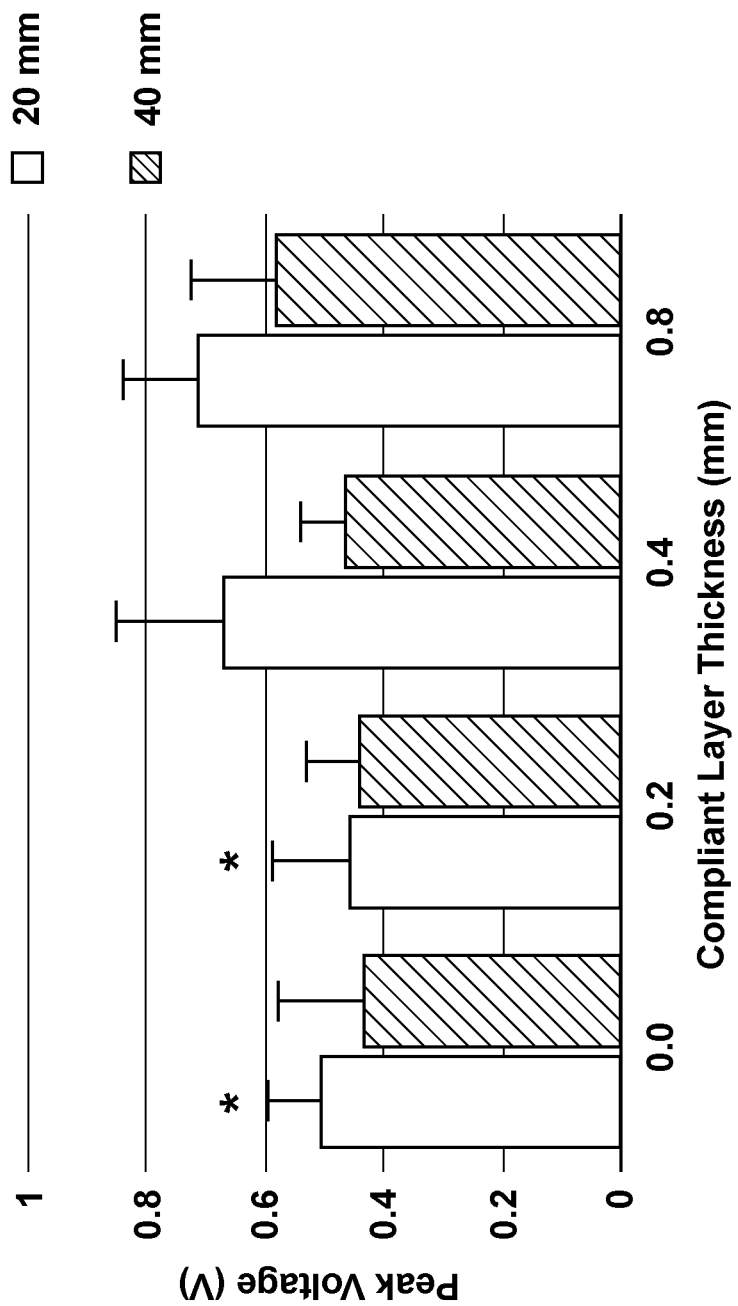
FIG. 10 shows average voltage output (n=5) as a function of distance and compliant layer thickness in water media for loading perpendicular to the PZT disc face. * represents significant difference from the 0.8 mm group at 20 mm (p<0.05).
Figure 11:
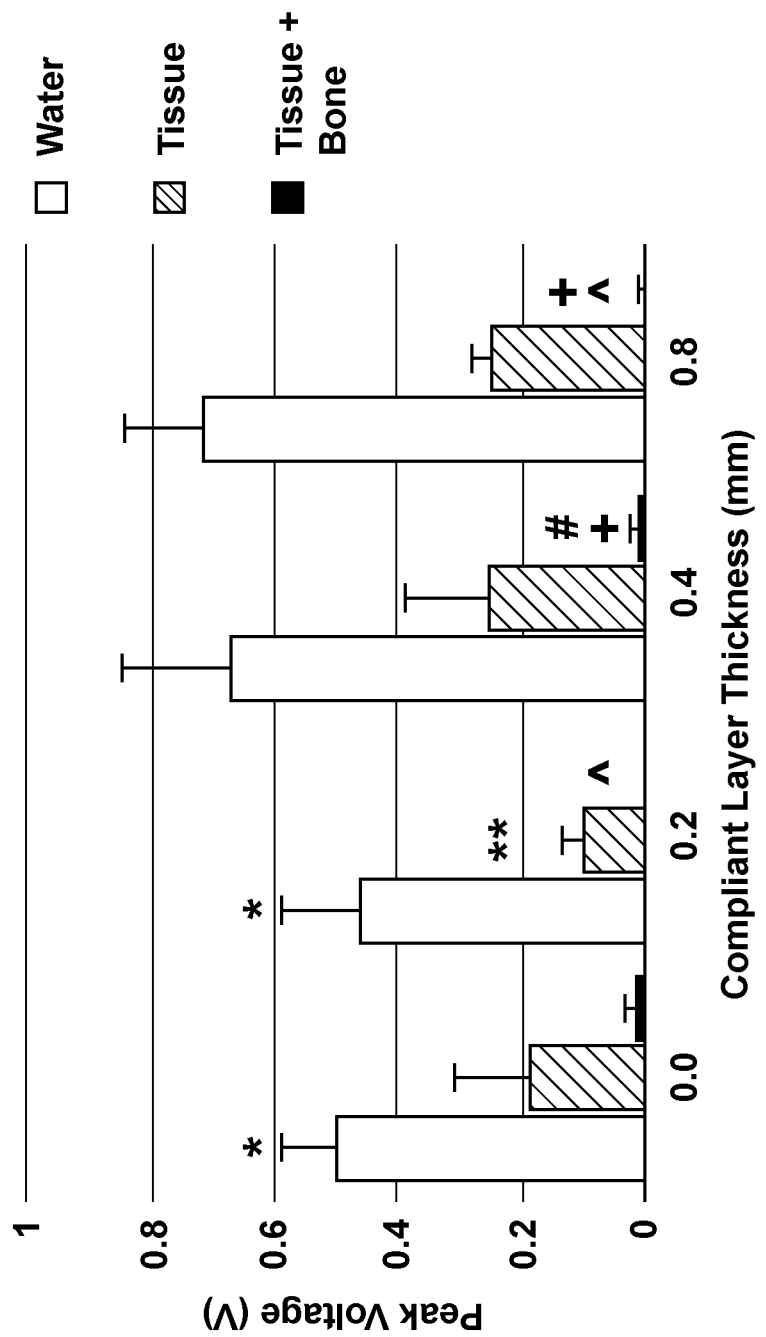
FIG. 11 shows average voltage output (n=5) as a function of media and compliant layer thickness at 20 mm distance for loading perpendicular to the PZT disc face. In water: * represents significant difference from 0.8 mm. In tissue: ** represents significant difference from 0.8 mm. In tissue plus bone: ^ represents significant difference from 0 mm, + represents significant difference from 0.2 mm, # represents significant difference from 0.8 mm (p<0.05).

Results: FIG. 10 shows the average voltage generated as a function of distance and compliant layer thickness in water. The two thicker compliant layer specimens yielded higher voltage outputs than the two with thinner layers. In addition, doubling the distance between the specimens and the probe reduced the voltage output by an average of 26%. FIG. 11 shows the average voltage generated as a function of media and compliant layer thickness. In water, the voltage output levels for all compliant layer thicknesses were significantly greater than tissue and tissue plus bone ($p<0.05$). The tissue and bone media had the lowest voltage output. In comparison to 20 mm of water media, the tissue and tissue plus bone yielded 67% and 98% less voltage on average, respectively.

Conclusions: The addition of a 0.4 or 0.8 mm compliant layer increased the ability of the PZT composite to produce electrical potential from a medical imaging ultrasound source which can then be rectified for use in DC bone stimulation applications. This effect is largest in water and tissue plus bone media.

Example 5: Effect of Compliant Layers in Piezoelectric Composites on Power Generation Providing Electrical Stimulation in Low Frequency Applications Materials and Methods CLACS Generation—Material Considerations The piezoelectric discs used were modified Navy Type I Lead Zirconate Titanate, PZT-4 material (SM111, STEMiNC, Doral, FL). Both the fired-on silver electrodes and electrical poling were completed by the manufacturer under controlled conditions. The discs were axially poled though the thickness (3-direction), with the positive and negative electrodes on the top and bottom faces. Because the discs were loaded axially in compression, the thickness poling direction would best utilize the power generation characteristics of the discs. The matrix material used was a room temperature cure, two-part, medical grade epoxy (EPO-TEK® 301, Epoxy Technology, Billerica, MA). In its cured state, EPO-TEK 301 has similar mechanical strength properties as common polymers used in implantable medical devices, and has desirable dielectric properties for use in a piezocomposite.

Specimen Fabrication

Figures 12A, 12B:
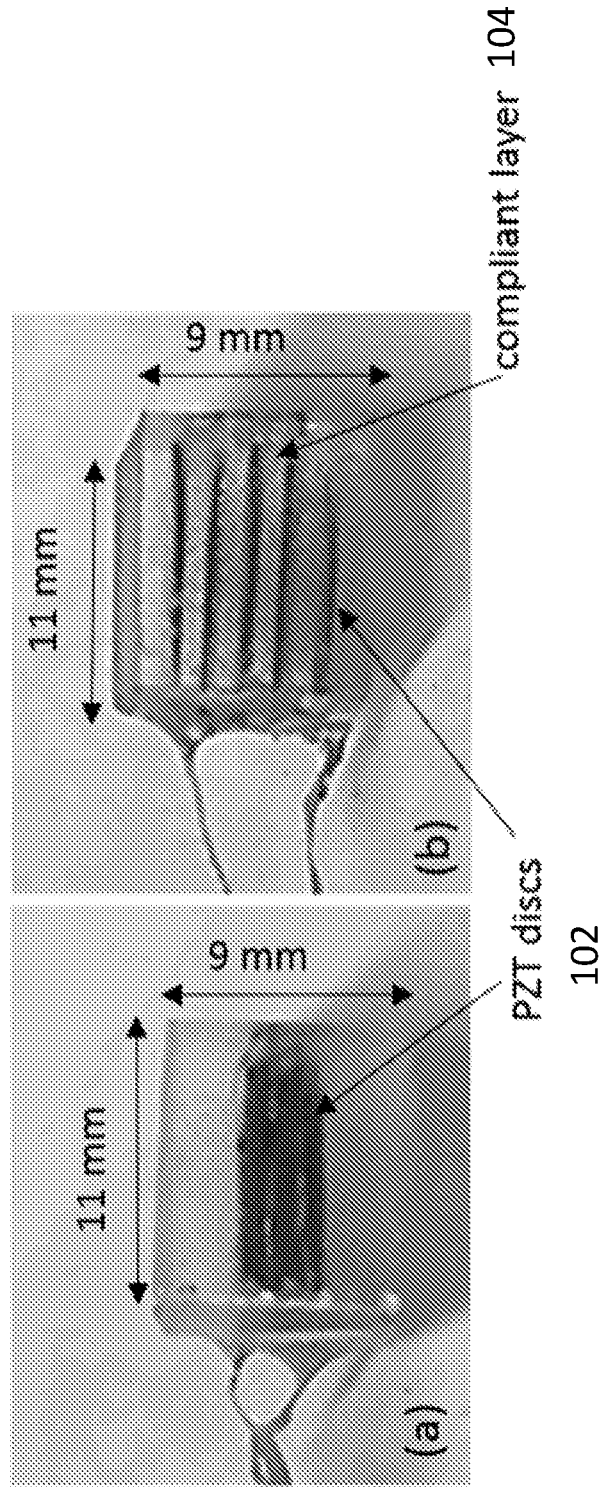
FIG. 12A shows a side view of a piezoelectric element layer stack with no compliant layer and FIG. 12B, a 0.8 mm compliant layer.

CLACS with three different compliant layer thicknesses (n=5 in each group) were fabricated using five 10×0.4 mm PZT discs and were encapsulated in epoxy, keeping volume of PZT, overall height, and surface area constant (FIGS. 12A and 12B). The five PZT discs were electrically connected in parallel using conductive epoxy (EPO-TEK® H20E, Epoxy Technology, Billerica, MA) and thin strips of copper foil. The positive poling direction of each disc was verified, and discs were connected in a chain. This connection method was used for its feasibility for modification with the compliant layers and ease of repeatability in a laboratory setting. The chains of PZT discs were folded in an accordion manner to create stacks mechanically in series. This resulted in alternating poling directions of the discs but maintained parallel electrical connection and separation of the positive and negative electrodes. Slices of 11×11 mm cured epoxy of varying thicknesses (0.4 and 0.8 mm±0.02 mm) were made to create the compliant layers. For the 0.0 mm CLACS group, a minimal amount of epoxy was used to adhere the discs together to create a stack. For the remaining groups, the compliant layers were adhered and interdigitated between the discs to create the CLACS. All stacks were encapsulated with EPO-TEK 301 to create 11×11×9 mm specimens. The volume of PZT (157 mm$^3$), volume of epoxy (932 mm$^3$), overall height and surface area were kept constant throughout all specimens. Electrical connectivity and system-level impedance was verified before each stack was electromechanically tested.

Electromechanical Testing

Specimens were electromechanically tested to compare voltage produced at varying mechanical loads, frequencies, and resistance loads. A 1200 N preload was applied, followed by cyclic compression at three peak-to-peak loads of 100 N, 500 N, and 1000 N at varying frequencies of 1 Hz, 2 Hz, 3 Hz and 5 Hz using an MTS MiniBionix 858 (MTS, Eden Prairie, MN) with a self-aligning plate and 2.5 kN load cell.

For each loading condition, voltage output of the stack was measured across a shunting resistance sweep ranging from 15 kΩ to 63.4 MΩ Resistance values were chosen to characterize the behavior of the stacks at lower resistances necessary for circuit design, as well as to capture the resonance behavior at the matched impedance. A sampling rate of 512 Hz was used for all test conditions and data was collected for 15 cycles to capture the steady-state behavior. The measured voltage was converted to RMS, VRMS=Vout/√2, and the average amplitude of the middle 5 cycles was used for power calculations. Power for each loading condition and resistance was calculated, P=VRMS2/R, and a two-way ANOVA was used to compare power production as a function of compliant layer thickness and resistance for each load. Tukey Kramer post-hoc analysis was performed to determine differences between groups ($\alpha$=0.05). The log transformation of the data was used to satisfy normality and equal variance assumptions.

Results

Power Generation

Figure 13:
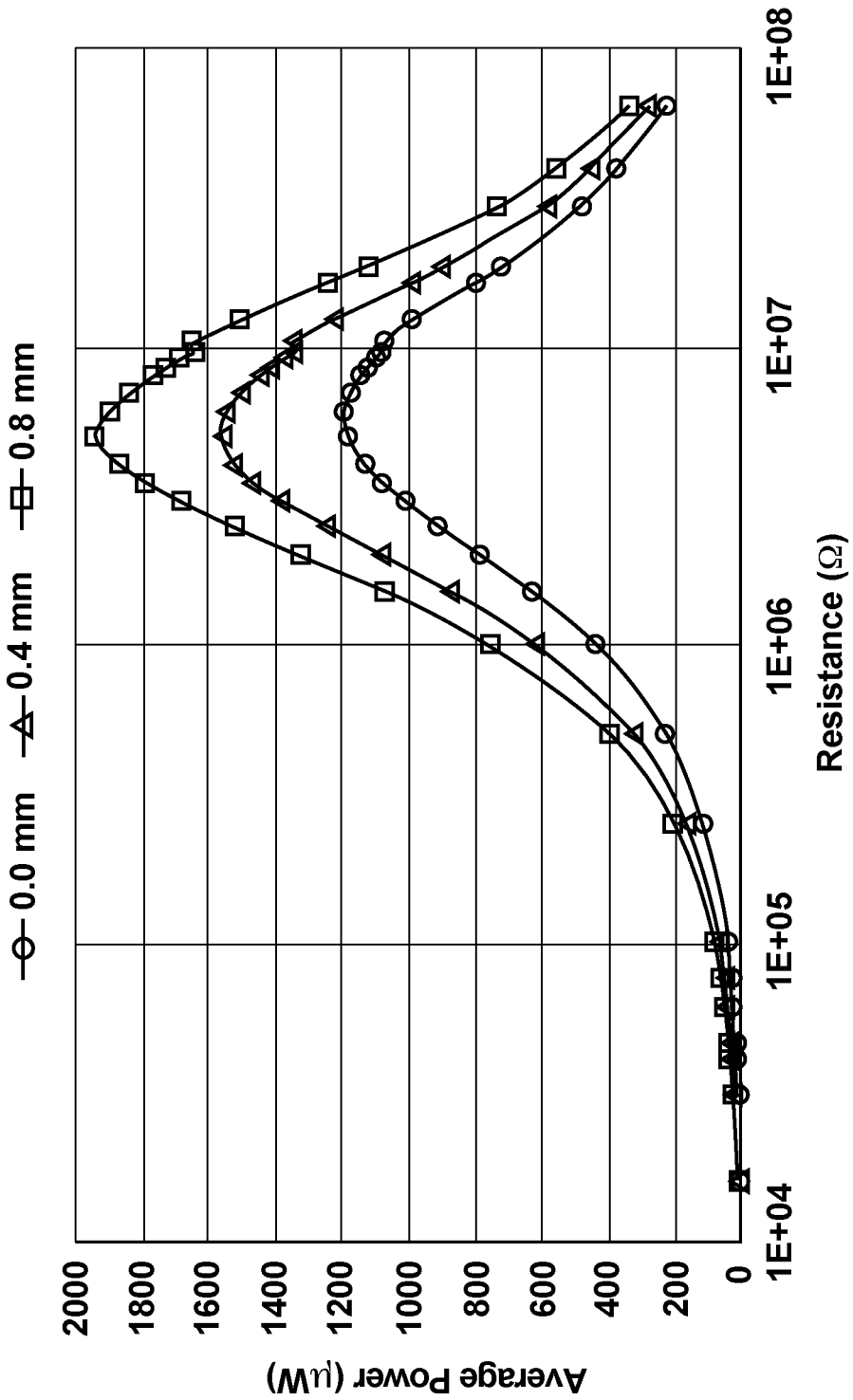
FIG. 13 shows average power output as a function of compliant layer thickness and resistance load. Average power generation curve for all groups at 1000 N and 2 Hz loading condition.

The power generation capability of each CLACS was characterized over a shunting resistance sweep of 15 kΩ to 63.4 MΩ FIG. 13 shows the average power generated as a function of compliant layer thickness for a 2 Hz, 1000 N sine wave input force, chosen to represent typical loading on an implant while walking. The shape of the power generation curve in FIG. 13 was consistent for all loads and frequencies tested. The addition of a compliant layer did not affect the source impedance, as each stack type exhibited maximum power at the same resistance (6 MΩ) for the 2 Hz frequency. Table 1 shows the effect of the compliant layer on overall maximum power output for each of the CLACS.

TABLE 1

Average maximum power output measured with respect to compliant layer thickness (1000N, 5 Hz, 2.5 MΩ)

| Compliant layer Thickness (mm) | Average Maximum Power (µW) |
| --- | --- |
| 0.0 | 3036 ± 267 |
| 0.4 | 3912 ± 708 |
| 0.8 | 4883 ± 813 |

As expected, maximum power generation occurred at the highest tested load and frequency (1000 N, 5 Hz) for all CLACS. Maximum power increased by 29% and 61% for the 0.4 mm and 0.8 mm groups respectively as compared to maximum power from the 0.0 mm baseline (p<0.0001). Additionally, the 0.8 mm group produced significantly more power than the 0.4 mm group with a 25% increase (p<0.0001). This relationship held true across all 12 loading conditions tested (p<0.05).

Frequency

Figure 14:
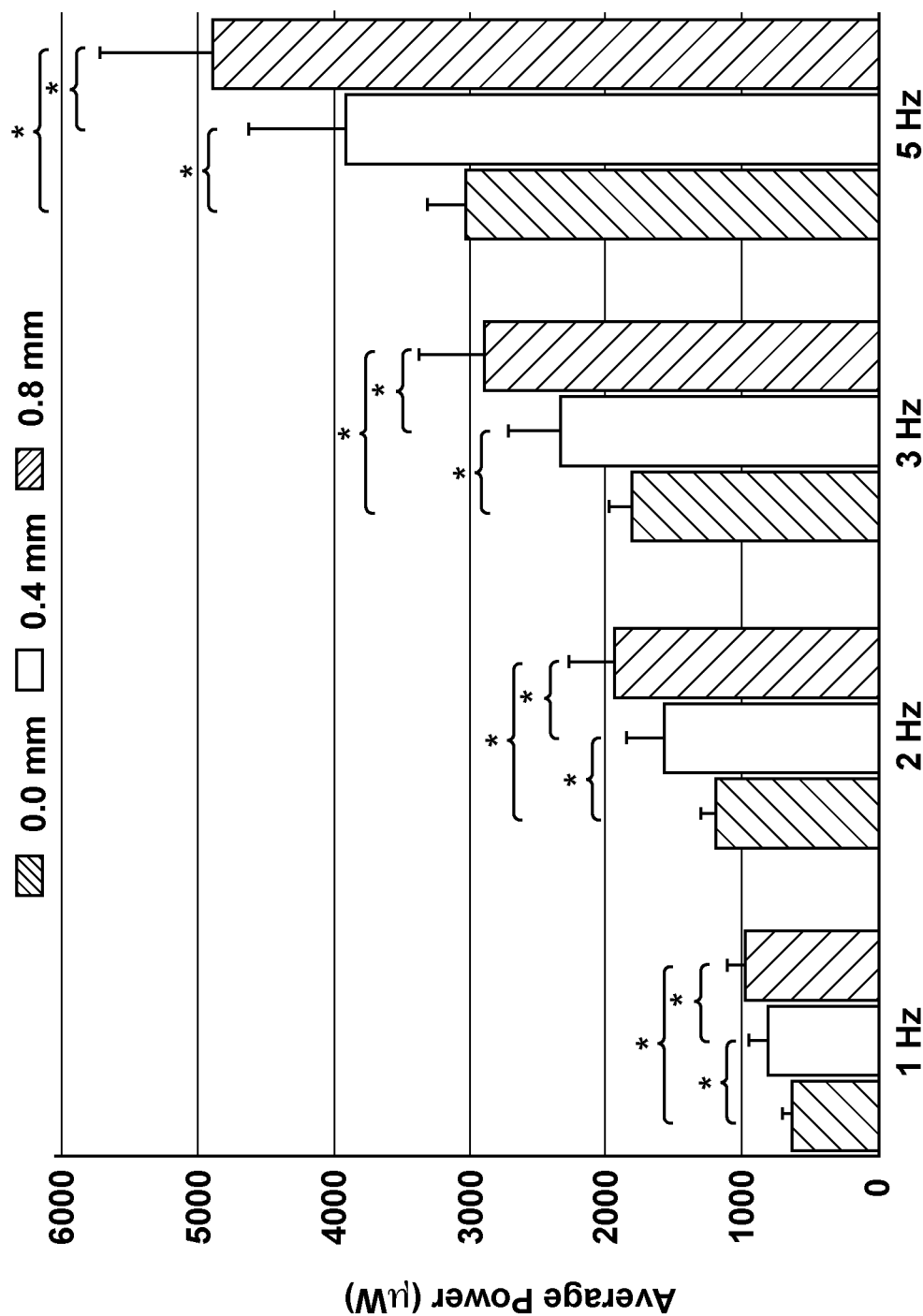
FIG. 14 shows average power generation as a function of compliant layer thickness and frequency at 1000 N. Average power presented at the resistance corresponding to peak power for each frequency (12 MΩ for 1 Hz, 6 MΩ for 2 Hz, 4 MΩ for 3 Hz, 2.5 MΩ for 5 Hz). * represents significant difference (p<0.05).

The average power generated for each stack type as a function of frequency and compliant layer thickness is shown in FIG. 14. Average power was reported at the resistance corresponding to maximum power for each frequency (12 MΩ at 1 Hz, 6 MΩ for 2 Hz, 4 MΩ for 3 Hz, 2.5 MΩ for 5 Hz). As frequency increased, average power occurred at a lower resistance. The statistical differences between compliant layer groups seen in the power generation curves and overall maximum power were consistent for all frequencies tested. The 0.4 mm and 0.8 mm CLACS produced significantly more power than the 0.0 mm CLACS for all frequencies (p<0.0001). The 0.8 mm CLACS also produced significantly more power than the 0.4 mm CLACS (p<0.0001). These results were consistent for all applied loads and all resistances. Additionally, an increase in frequency significantly increased power output for all groups (p<0.05). At each given load level tested, the increase in power generation due to the increasing frequency was primarily linear, with a two-fold increase from 1 to 2 Hz, a three-fold increase from 1 to 3 Hz, and a five-fold increase from 1 to 5 Hz. These relationships were consistent for all CLACS types for all compliant layer thicknesses for the load levels, resistances, and frequencies tested.

Load

Figure 15:
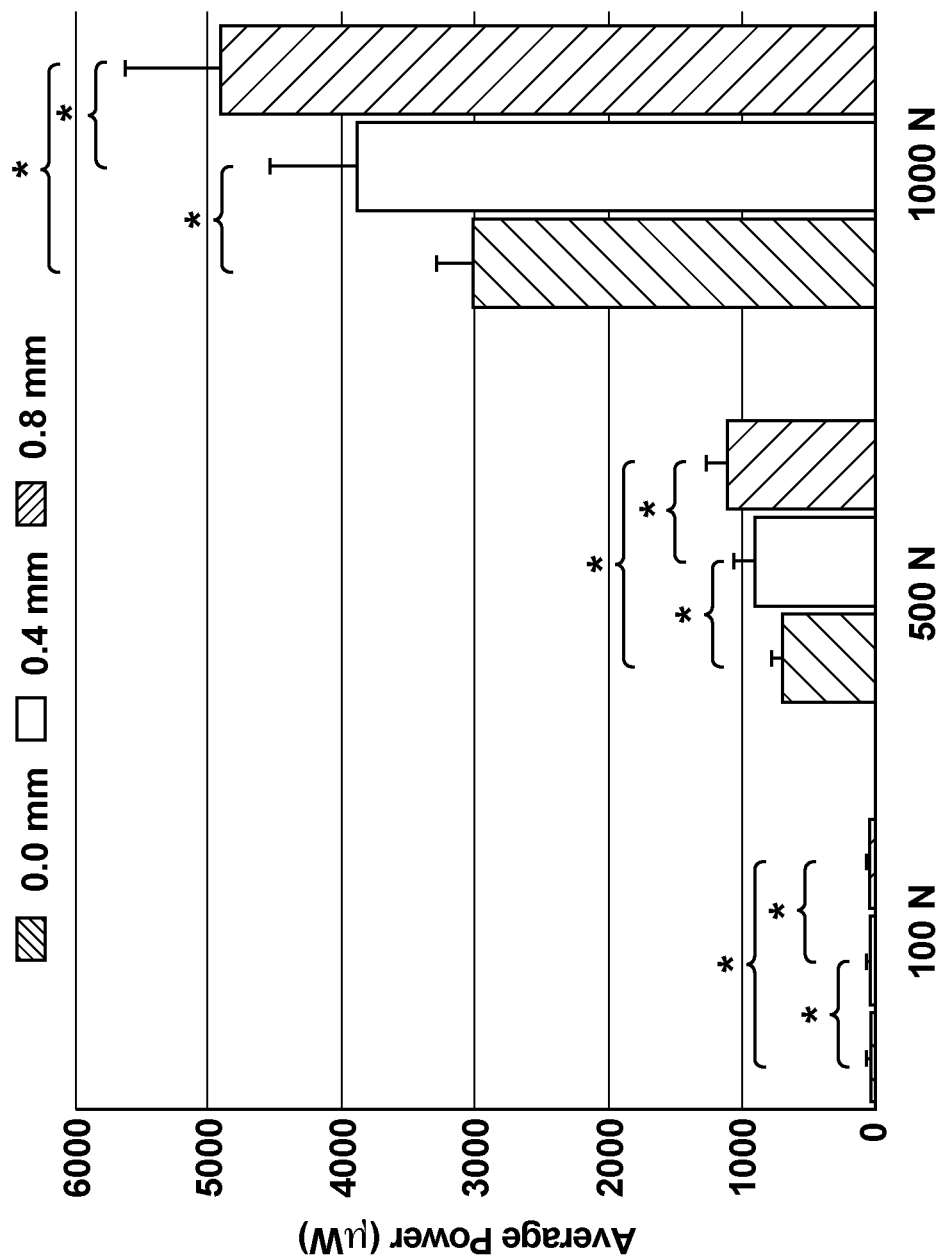
FIG. 15 shows average power as a function of compliant layer thickness and load at 5 Hz and 2.5 MΩ. * represents significant difference (p<0.05).

Increased mechanical load levels significantly increased power output for all groups (p<0.05). With the increase in load, there was a consistent percent increase in power for all frequencies, resistances, and CLACS type. At a given frequency, the maximum power generated was approximately 100 times greater with an increase from 100 N to 1000 N, approximately 27 times greater with an increase from 100 N to 500 N, and approximately 4 times greater with the increase from 500 N to 1000 N. This nonlinear increase was consistent throughout all specimens and loading conditions. FIG. 15 demonstrates the relationship of average power generation as a function of compliant layer thickness and mechanical load applied at 5 Hz and 2.5 MΩ. At 5 Hz, maximum power generation occurred at 2.5 MΩ for all CLACS types. The statistical relationships between compliant layer groups were the same in varying loads as with frequency variation. Both the 0.4 mm and 0.8 mm compliant layer thickness CLACS produced significantly more power as compared to the 0.0 mm (p<0.0001), and the power generated from the 0.8 mm CLACS was significantly greater than 0.4 mm CLACS (p<0.0001).

Discussion

This study was designed to investigate the feasibility of CLACS for use in enhancing power generation under human motion loading, specifically for use in implantable orthopedic devices to increase bone healing with DC stimulation. The goal was to measure the effect of compliant layers between PZT discs and quantify increased efficiency in harvesting energy at low frequencies due to increasing compliant layer thickness. The loads and frequencies tested in the present study define the power generation capability of CLACS under conservative estimates of loading in generic orthopedic implants, but there are other off-resonance frequencies and applications (i.e. civil infrastructure) for which CLACS could be used as an efficient energy harvesting mechanism.

The results of this study showed that there was a significant increase in power due to compliant layers between PZT discs in a stack at all loads and frequencies, and across all resistances measured. The addition of the compliant layer between each PZT disc increased the positive strain in the in-plane directions of the disc while compressive loads are applied to the stack in the through-thickness direction, thus effectively amplifying the piezoelectric effect of the material and increasing the voltage (and power) produced.

The CLACS structure described herein increased efficiency and lowered the source impedance at maximum power while maintaining the tough mechanical properties. Both attributes are important in medical implants and devices subjected to relatively low frequency loading conditions, e.g., at 1000 N and 2 Hz, a loading condition that mimics loads in the spine during walking. With the volume of PZT (157 $mm^3$), the 0.0 mm, 0.4 mm, and 0.8 mm CLACS, generated 804 µW, 991 µW, 1243 µW respectively under the disclosed loading conditions and applied resistance. Additionally, the maximum power from all CLACS groups occurred at 5 MΩ, significantly lowering the source impedance and producing more power at every applied resistance. The addition of the compliant layer did not change the resistance at which maximum power was generated. It is important that a DC signal is delivered to the desired bone healing site, so the alternating signal produced by the piezoelectric material must be conditioned and rectified. This rectification circuit would ideally be very small, meaning it would also have a small resistance. The ability of the CLACS to produce significantly more power than traditional stacks at lower resistances is beneficial for medical device design.

Conclusions

The addition of a compliant layer between PZT discs to form CLACS significantly increased the power production capabilities of PZT stacks across all compressive mechanical loading conditions and resistances, while PZT volume remained constant. The use of compliant layers in piezoelectric stacks for power generation provides an effective method for energy harvesting, without the use of a battery, in low frequency applications.

Example 6: Power Generation Amplification and Stack Toughening Via Compliant Layer Interdigitation Experimental Methods To investigate the effect of toughening piezoelectric stacks by adding compliant layers in between the discs, CLACS were manufactured. Compliant layers were sliced from cured EPO TEK 301 epoxy (Epoxy Technology, Billerica, MA) in two different thicknesses 0.4 mm±0.02 mm and 0.8 mm±0.02 mm. These thicknesses were chosen based on the thickness of the PZT discs used. 10×0.4 mm modified PZT-4 (SM111) discs were chosen for the favorable coupling coefficient (0.45) and sizes that would allow efficient manufacturing in the laboratory. Chains of five PZT discs (STEMiNC, Doral, FL) were connected using copper foil and EPO-TEK H20E conductive epoxy (Epoxy Technology, Billerica, MA), ensuring parallel electrical connectivity. CLACS were created by adhering the compliant layers in between each of the PZT discs, alternating the poling direction of each adjacent disc (FIG. 5A). Stacks without a compliant layer (0.0 mm group) were also manufactured as a control for comparison. The 0.0 mm stacks were electrically connected and stacked with a single droplet of epoxy to ensure proper alignment once encapsulated. Each CLACS type (n=5 in each group) were encapsulated in EPO-TEK 301, ensuring that the overall volume (11×11×9.5 mm) remained constant (see FIG. 12B).

Following the manufacturing of the CLACS, electromechanical testing was completed to characterize the power production capabilities of each stack type. Pure compressive loads were applied using an MTS MiniBionix 858 (MTS, Eden Prairie, MN) with a self-aligning platen. The loading conditions were chosen to characterize the effect of the compliant layer as a function of three loads and four frequencies. Following a 1200N compressive preload, a cyclic load of 100N was applied for 15 cycles at each frequency tested (1 Hz, 2 Hz, 3 Hz and 5 Hz). The same procedure was followed for a 500N and 1000N load at each frequency. All four frequencies tested were chosen to be well below the resonant frequency (5 MHz) of the PZT discs. For each load and frequency combination, steady state voltage output from each CLACS was measured across a shunt resistance sweep from 15 kΩ to 63 MΩ. The measured voltage was converted to RMS, scaled to reflect voltage output of the CLACS, and the average amplitudes of the middle five cycles was used for the voltage and power comparisons. For each load, frequency and resistance, power output was calculated. Results were compared using a two-way ANOVA with a Tukey-Kramer post-hoc analysis ($\alpha=.05$).

Experimental Results

All CLACS groups were experimentally tested and average voltage and power output as a function of compliant layer thickness and optimal load resistance can be seen in Table 2. The optimal load resistance for all groups was 2.5 MΩ (1000N, 5 Hz). For all loading conditions tested, an increase in compliant layer thickness significantly increased power generation (p<0.0001). The 0.8 mm group produced on average 61% and 25% more power than the 0.0 mm and 0.4 mm groups, respectively. Similarly, the 0.4 mm group produced 29% more average power than the 0.0 mm group. Voltage significance follows the same statistical trends (p<0.05), with an 11% increase due to the 0.4 mm thickness as compared to the 0.0 mm group, and an 26% increase due to the 0.8 mm thickness compared to the 0.0 mm group. There was no statistical difference between voltage produced by the 0.4 mm and 0.8 mm groups at this specific load, frequency and resistance (p=0.08).

TABLE 2

Average peak power and voltage output of
each CLACS group at 1000N, 5 Hz, 2.5 MΩ.

| Compliment Layer Thickness (mm) | Average Voltage at Maximum Power (V) | Average Maximum Power (μW) |
|---|---|---|
| 0.0 | 87.1 ± 3.8 | 3036 ± 267 |
| 0.4 | 98.3 ± 8.1 * | 3912 ± 708 * |
| 0.8 | 110.0 ± 8.4 * | 4883 ± 813 *# |

\* represents significant difference from 0.0 mm group.
\# represents significant difference from 0.4 mm group.

Figure 16:
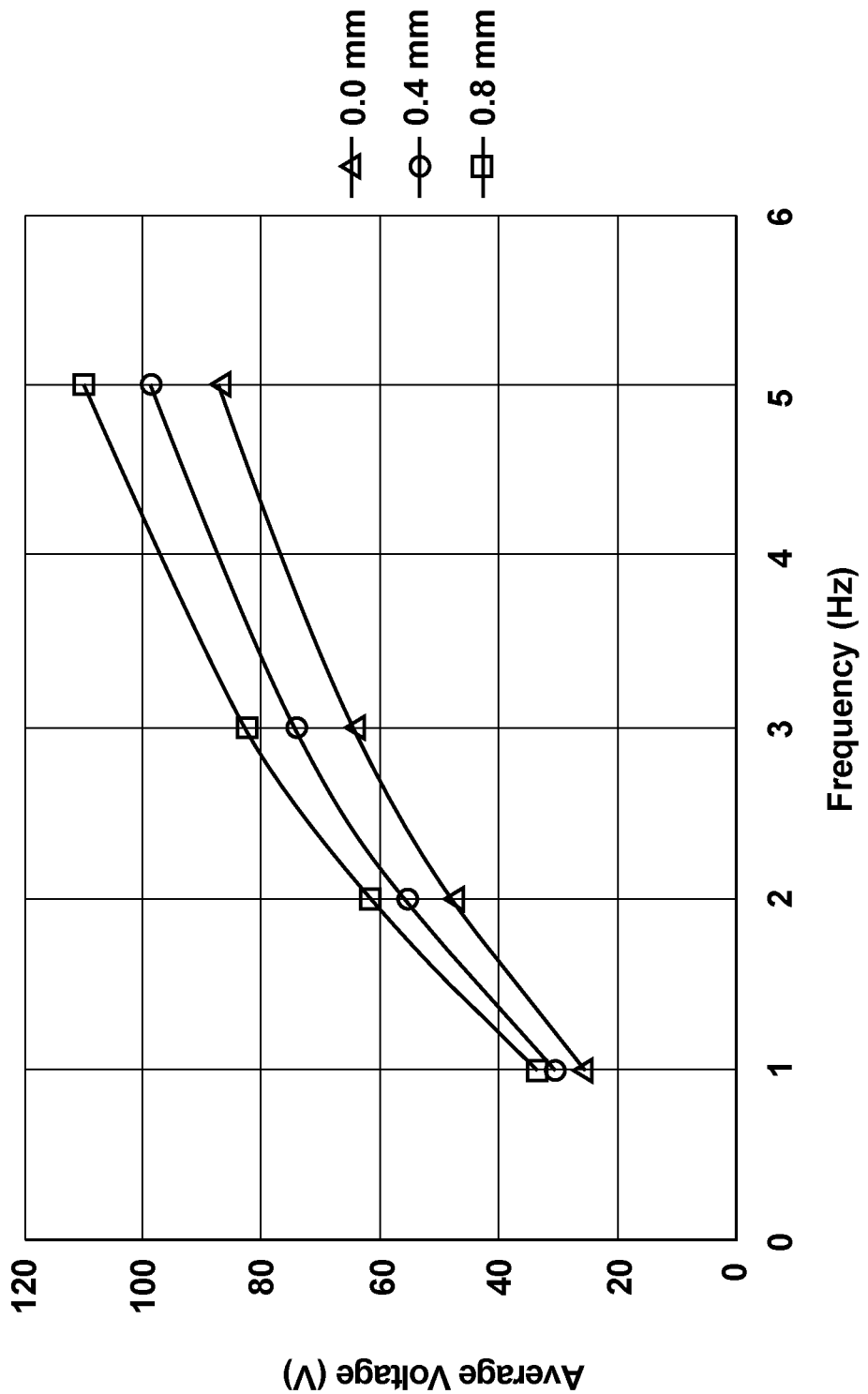
FIG. 16 shows average voltage as a function of compliant layer thickness and frequency. Representative voltage data presented at maximum power (1000N, 2.5 MΩ).

The average voltage produced as a function of frequency and compliant layer thickness is shown in FIG. 16. Results are presented at optimal resistance for all groups. Average voltage produced by the CLACS increased with increasing frequency. With increasing frequency, an increase in compliant layer thickness has a larger effect on voltage output. The 0.4 mm group produced on average 11% more voltage compared to the 0.0 mm group and the 0.8 mm group produced on average 23% and 11% more voltage than the 0.0 mm and 0.4 mm groups, respectively ($p<0.05$). These statistical trends and percent changes were consistent for all four frequencies tested. The nonlinearity of the voltage-frequency relationship suggests that the increase in voltage due to the compliant layer is most effective at low frequencies.

Figure 17:
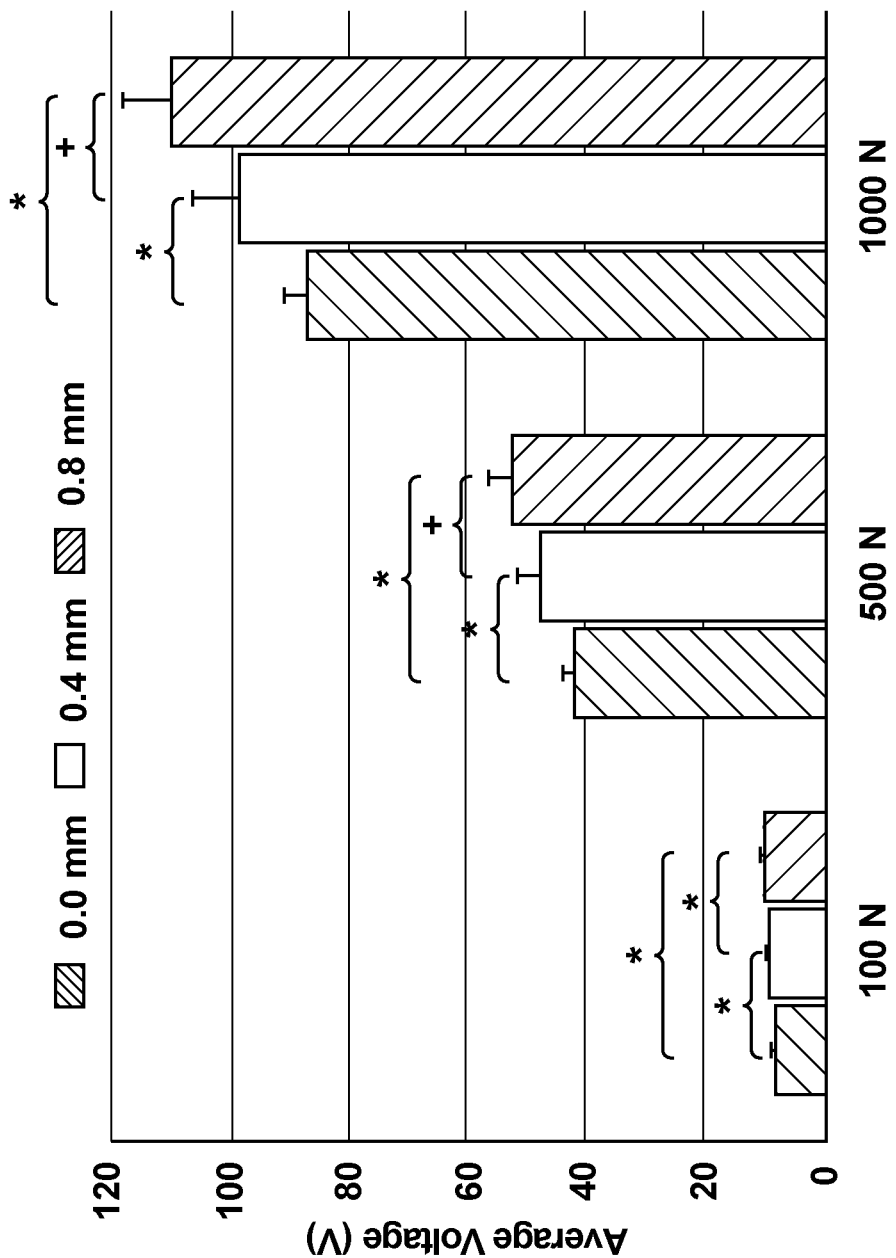
FIG. 17 shows average voltage as a function of compliant layer thickness and pure compressive load applied. Representative voltage data presented at 5 Hz and 2.5 MΩ. * represents significant difference (p<0.05). + represents trend toward significant difference (p<0.1).
Figures 19A, 19B, 19C, 19D, 19E, 19F:
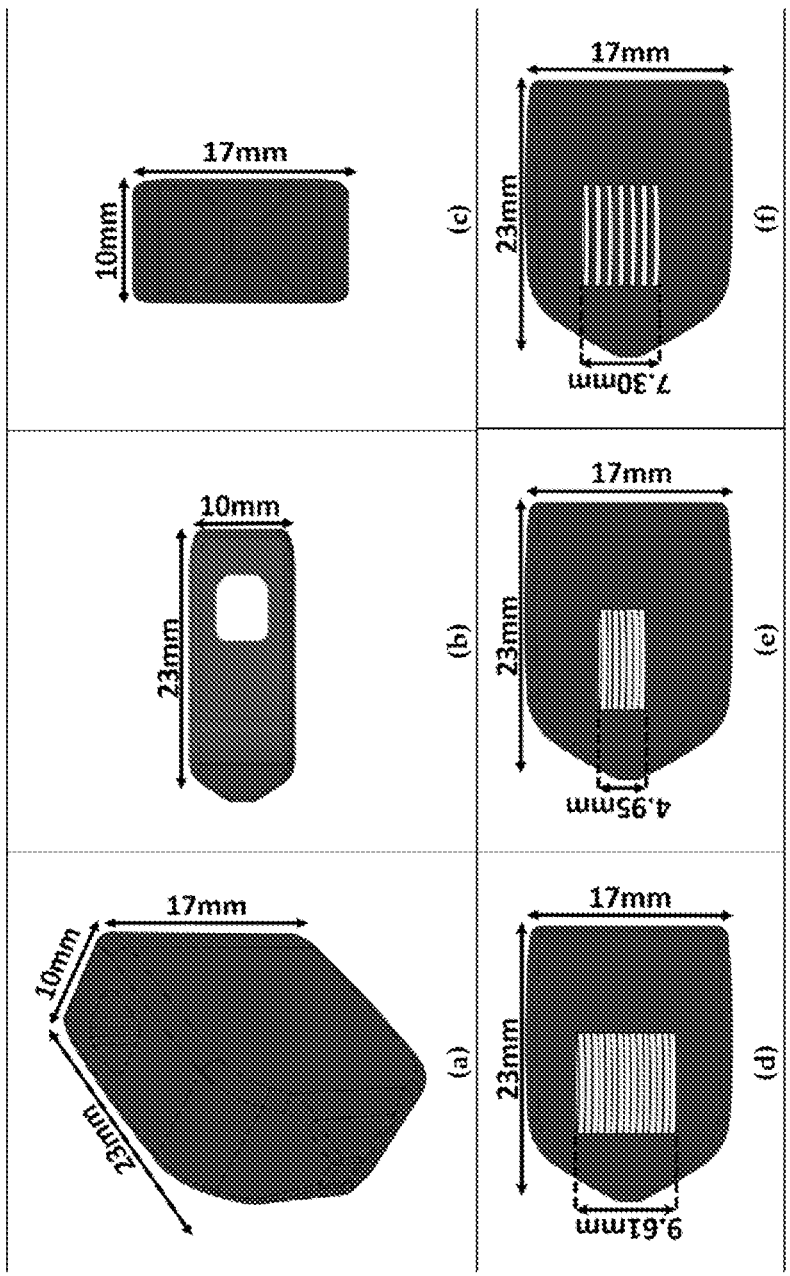
FIG. 19A-19F show an implant schematic. The 23×10×17 mm TLIF implant A) isometric view, B) top view, C) front view, D) side view with the 15-disc insert, E) side view with the 7-disc insert, and F) side view with the 7-disc CLACS (Compliant Layer Adaptive Composite Stack) insert. The outer shape remained constant regardless of insert type.

Additionally, an increase in load significantly increased voltage produced for all groups ($p<0.05$), as seen in FIG. 17. Specifically, an increase in load from 100N to 500N led to a 4.7-fold increase for all groups, 500N to 1000N led to a 2.2-fold increase, and 100N to 1000N led to a 10.5-fold increase in voltage produced. At 100N, an increase in compliant layer thickness significantly increased voltage produced ($p<0.05$). At 500N and 1000N, the 0.4 mm and 0.8 mm groups both produced significantly more voltage as compared to the 0.0 mm group ($p<0.05$), and were trending toward a significant difference from each other ($p<0.1$).

The mass power density as a function of compliant layer thickness and load applied can be seen in FIG. 18. This increase in mass power density as a function of applied load was found for all frequencies and resistances tested. Again, an increase in compliant layer thickness increased the mass power density. Additionally, with an increase in load applied, the effect of compliant layer on mass power density was consistent.

Example 7: Stacked Piezoelectric Discs Generate Necessary Power for Bone Healing Through Electrical Stimulation in a Composite Spinal Fusion Implant The aim of this study was to evaluate electromechanical properties of three composite PZT disc stacks as inserts within a spinal interbody implant and validate their use as a generator for electrical stimulation: 1) 15-disc implant; 2) 7-disc implant; 3) 7-disc CLACS implant.

Materials and Methods

Implant Design

The implant size and shape chosen for this study was modeled after a transforaminal lumbar interbody fusion (TLIF) implant previously cleared by the FDA with dimensions of 23×10×17 mm and a graft window of 5×5.5×17 mm (FIG. 19A-19F). This configuration represents the aspect ratio of height to footprint that corresponds to mechanical worst-case typically used in mechanical testing for FDA clearance. The total volume of the implant was calculated to be 3,013.95 mm$^3$ using the SOLIDWORKS mass properties tool. A mold of the implant was made using a to-scale 3D printed replica and high performance liquid silicone (Dragon Skin 10, Smooth-On, Macungie, PA).

Piezoelectric Composite Material Fabrication

Three different piezoelectric inserts (n=6 for each insert type) were made using pre poled and electroded 7×0.4 mm discs of modified PZT-4 (Lead Zirconate Titanate, SMD7T04R111, STEMiNC, Doral, FL). The diameter of the discs was chosen to fit within the front end of the implant while maximizing the ratio of PZT surface area to implant surface area. The number of PZT discs was chosen such that the three different inserts could fit in all TLIF implant configurations with heights ranging from 11 mm to 17 mm.

The first configuration was a 15-disc insert—15 PZT discs connected electrically in parallel and stacked mechanically in series. The second configuration was a 7-disc CLACS insert—7 PZT discs connected electrically in parallel and stacked mechanically in series with a 0.4 mm compliant layer of matrix epoxy between each disc (see FIG. 2B). The 0.4 mm±0.02 mm compliant layers of matrix epoxy were cut using a precision section saw. The final configuration was a 7 disc insert—7 discs connected electrically in parallel and stacked mechanically in series. All discs were connected electrically in parallel using two strips of copper foil 0.02 mm in thickness (Basic Copper, Carbondale, IL) and silver conductive epoxy (EPO-TEK H20E, Epoxy Technology, Billerica, MA) with a 100° C. cure for 2 hours. The discs were then stacked mechanically in series using a medical grade matrix epoxy and inspected to ensure mechanical bond between all layers (EPO-TEK 301, Epoxy Technology, Billerica, MA). The matrix epoxy was cured at room temperature for 24 hours followed by a 2 hour cure at 65° C. to ensure crosslinking of the material.

Once fully cured, each insert was placed inside the silicone mold (Dragon Skin 10 Medium, Smooth-On, Macungie, PA) on top of a 7×7×4 mm slice of cured matrix epoxy to ensure a uniform distance from the bottom of the implant for all samples. The end of each copper strip was fed through a small horizontal slit at the front end of the implant in the silicone molds. The molds were then filled with the medical grade matrix epoxy (EPO-TEK 301, Epoxy Technology, Billerica, MA). This epoxy was chosen to encapsulate the implants due to its similarity in storage modulus to PEEK (polyether-ether-ketone). The implants were cured at room temperature for 24 hours, then removed from their molds and oven cured at 65° C. for 2 hours.

Electromechanical Testing

To simulate physiological loading conditions in the lumbar spine, each implant was subjected to a pure compressive 1200N preload followed by peak-to-peak cyclic load of 1000N at 2 Hz for 15 cycles using an MTS MiniBionix 858 (MTS, Eden Prairie, MN) with a sampling frequency of 512 Hz. The 2 Hz frequency was chosen to best represent normal human gait. The voltage was measured across 31 different applied resistances in series with the implant ranging from 16.0 kΩ to 63.4 MΩ to fully characterize the voltage and power capabilities of the implants. The loading and frequency profiles were chosen to represent loads experienced between vertebral bodies in the lumbar spine with posterior instrumentation under normal human walking.

Data Analysis

Customized MATLAB software (Mathworks, Natick, MA) was used to calculate power produced by each implant from the measured voltages. The average maximum voltage was calculated using a voltage divider from the amplitude of the middle five loading cycles and scaled by the corresponding applied resistive load (Rapplied) and the 2 MΩ resistance of the MTS (RMTS).

To calculate the power produced by each implant, the voltage was converted to RMS then power was calculated using Joule's Law.

To calculate power density, the power was divided by the total volume of PZT material for each implant. A two-way ANOVA with a Tukey-Kramer post-hoc analysis was used to determine statistical significance between power and power density produced by three implant types at each applied resistance ($\alpha=0.05$). A one-way ANOVA with a Tukey-Kramer post-hoc analysis was used to determine the effect of implant type at 30 MΩ, the resistance of the rectifying circuit used in the pilot ovine study to transform the signal from AC to DC ($\alpha=0.05$).

Results

Figure 20:
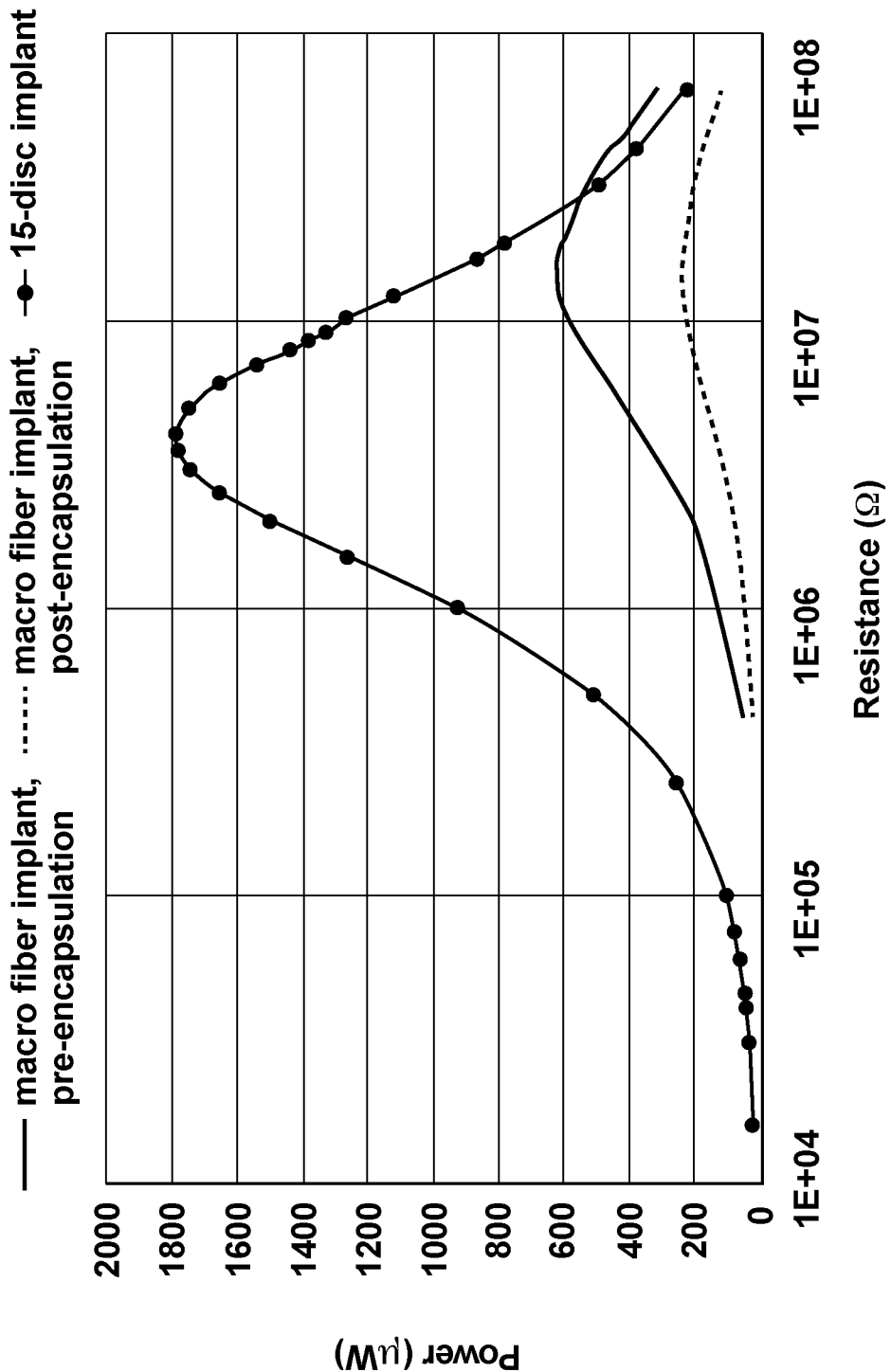
FIG. 20 shows power comparison between PZT fibers and PZT discs. Power generated by the composite macro fiber implants from Goetzinger et al. (pre-encapsulated implant) (Goetzinger, N. C.; Tobaben, E. J.; Domann, J. P.; Arnold, P. M.; Friis, E. A. Composite piezoelectric spinal fusion implant: Effects of stacked generators. J. Biomed. Mater. Res. B Appl. Biomater. 2016, 104, 158-164) and Tobaben et al. (post encapsulated implant) (Tobaben, E. J.; Goetzinger, N. C.; Domann, J. P.; Barrett-Gonzalez, R.; Arnold, P. M.; Friis, E. A. Stacked macro fiber piezoelectric composite generator for a spinal fusion implant. Smart Mater. Struct. 2015, 24) compared to the TLIF implant with a 15 disc insert. For similar PZT volume and cross-sectional area ratio, the composite 15-disc implant outperformed the macro fiber implants.

The average power output from the 15-disc implants was compared to previous studies that assessed power production from a composite TLIF throughout the manufacturing process. The total volume of PZT in the macro fiber implants was 217 mm$^3$. This is very similar to the 230 mm$^3$ volume of PZT in a 15-disc, traditional implant. Across the resistance sweep, the 15-disc implant outperformed both the pre encapsulated and post encapsulated TLIF implants (FIG. 20). The ratio of PZT cross-sectional area to footprint surface area for the pre-encapsulation and post-encapsulated macro fiber implant was 30% and 16% respectively as compared to 27% for the disc implants. The PZT disc implants generated more power compared to the macro fiber implant for similar PZT volumes and cross-sectional area to footprint ratios. This was due to the increased number of layers connected electrically in parallel which lowered source impedance of the insert and improved materials and manufacturing methods.

The 7-disc CLACS were manufactured to address potential deficits in mechanical properties with the brittle nature of the 15-disc implants. The power for the 7-disc CLACS implants was compared to both the 15-disc implants and the 7-disc implants. The 7-disc implants and 7-disc CLACS implants had identical PZT volume and surface area ratios. As expected, the power increased as applied resistive load increased until the applied resistive load matched the impedance of each implant, demonstrating maximum power output for each implant. Table 3 summarizes the voltage and applied resistive load corresponding to maximum power produced by each implant configuration. A two-way ANOVA was used to determine the effect of implant type and applied resistance on power. The log transform of power was used to satisfy normality and variance requirements for this analysis. The interaction between implant type and applied resistance was significant (p<0.01), indicating that the effect of resistance on power generated depends on the type of implant. As resistance increased, the effect of insert type decreased (p>0.05).

TABLE 3

Average maximum power and voltage ± standard deviation.

| Implant Type | Average Maximum Power (μW) | Average Voltage at Maximum Power (V) | Applied Resistive Load for Maximum Power (MΩ) |
| --- | --- | --- | --- |
| 15-disc insert | 1789 ± 540 | 84 ± 12 | 4 |
| 7-disc insert | 294 ± 90 | 54 ± 9 | 10 |
| 7-disc CLACS insert | 935 ± 261 | 96 ± 14 | 10 |

Figure 21:
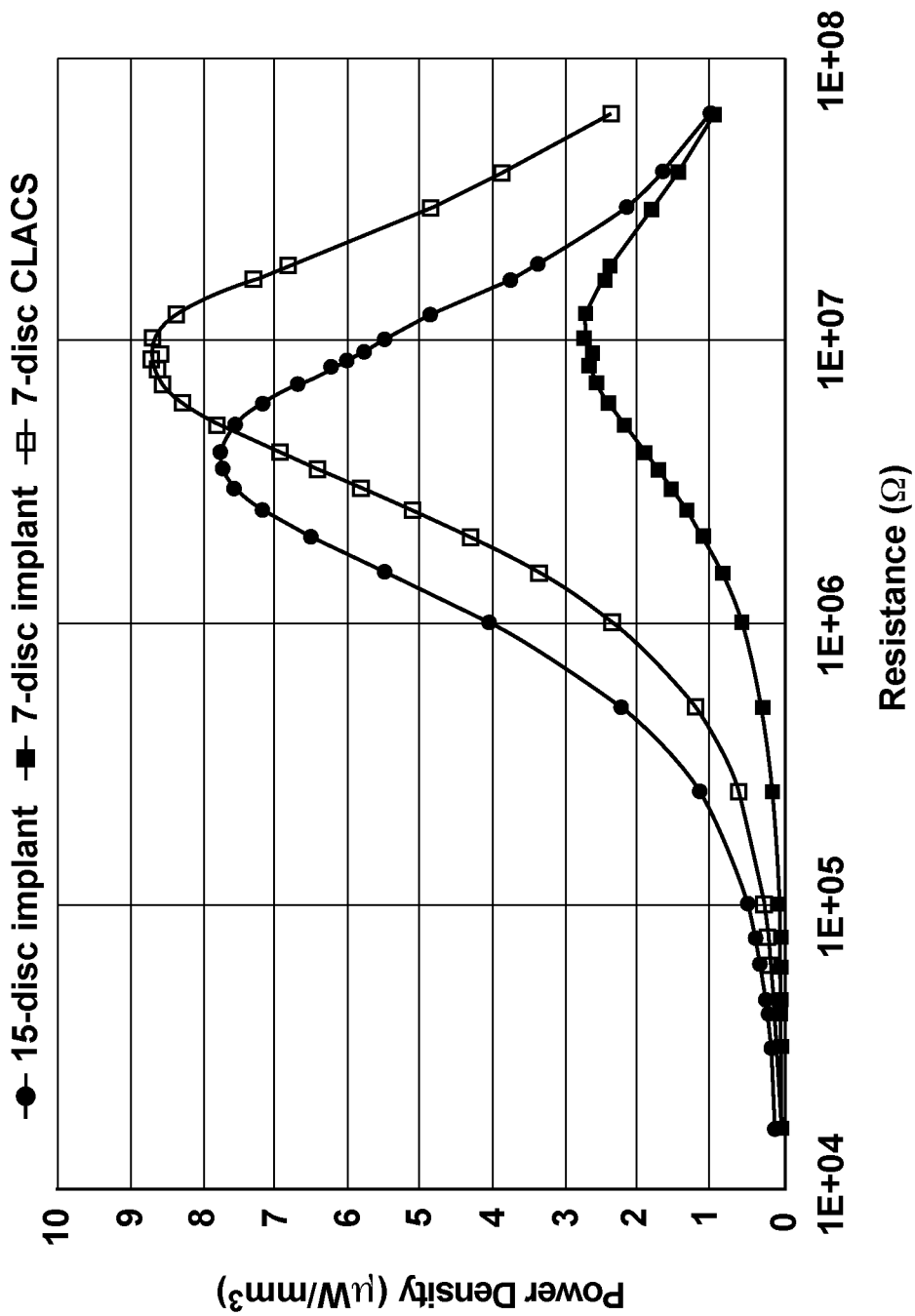
FIG. 21 shows power density as a function of applied resistance and PZT disc implant type. Power density (power normalized by volume of PZT for each implant type) generated for the three implant configurations across an applied resistive load from 16.0 kΩ to 63.4 MΩ.
Figure 22:
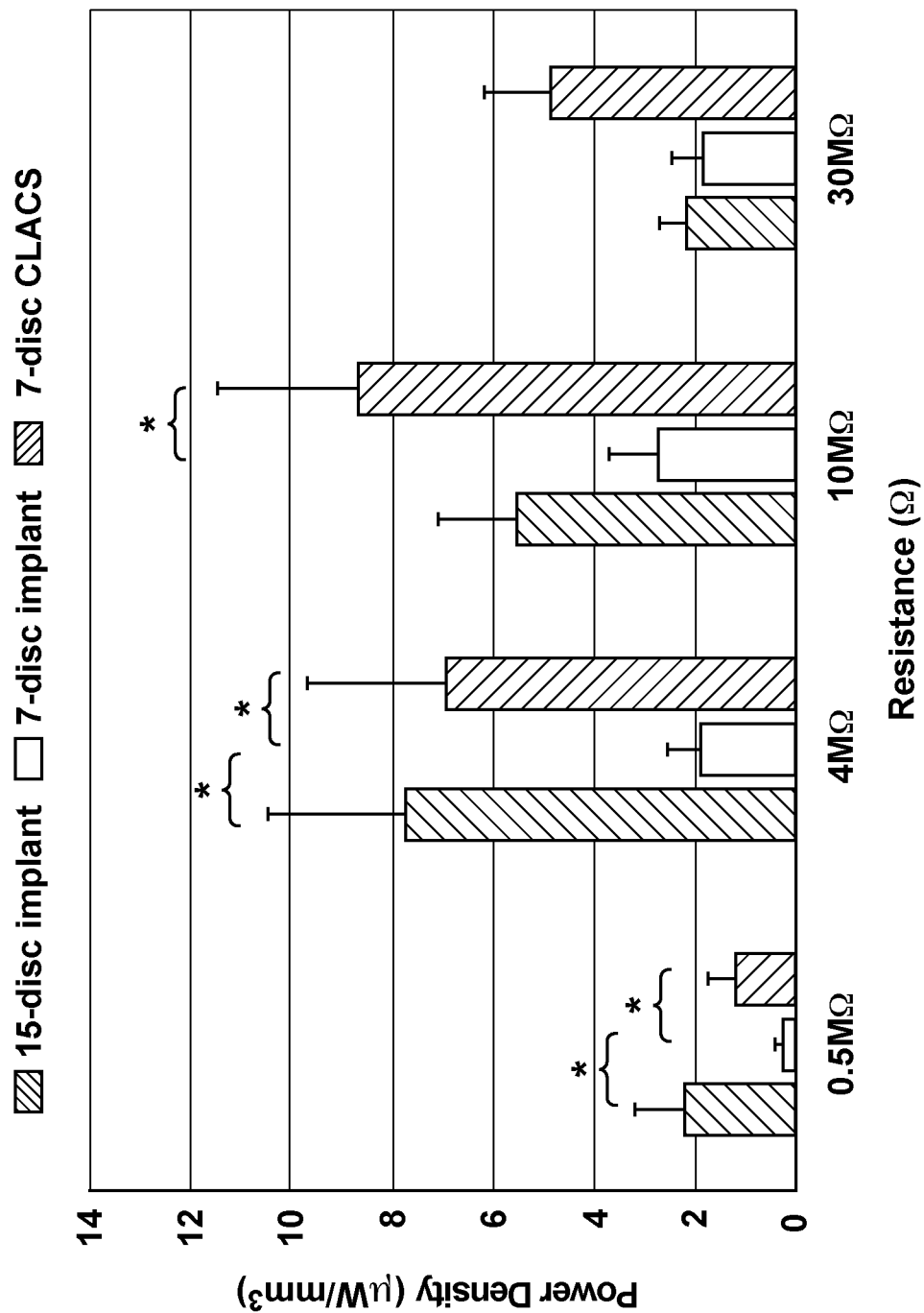
FIG. 22 shows power density comparison between PZT disc implants. Power density (power normalized by volume of PZT for each implant type) generated for the three implant configurations (15-disc implant, 7-disc implant, and 7-disc CLACS implant) at a low applied resistive load (0.5 MΩ), resistance of maximum power for the 15-disc implant (4 MΩ), resistance of maximum power for both 7-disc implants 10 MΩ, and a high applied resistive load (30 MΩ). * represents significant difference (p<0.05).

To compare power across implants with different insert types, the power was normalized by the total PZT volume to obtain power density for each implant configuration (FIG. 21). While maximum power occurred at the lowest resistive load for the 15-disc implant, the maximum power density was greatest for the 7-disc CLACS implant. The 15-disc implant had the largest power density at resistances lower than 4 MΩ, the resistance corresponding to its maximum power. FIG. 22 illustrates the power density of each implant at 0.5 MΩ, 4 MΩ, 10 MΩ, and 30 MΩ corresponding to a low applied resistance, resistance at maximum power for the 15-disc implant, resistance at maximum power for both 7-disc implant types, and a high applied resistive load respectively. As resistance increased, the effect of implant type on power density decreased following the same statistical trend as the power results.

Discussion

This study assessed the power producing capabilities of PZT stacked disc inserts in a TLIF implant cage under physiological loads present in the lumbar spine, demonstrating that they can provide the necessary power needed to stimulate bone growth.

The TLIF interbody implant design used in this study had a defined length and width of 17×10 mm but a variable height of 11 mm to 17 mm. To streamline future manufacturing of all implant size iterations, one defined PZT insert size is to be chosen to fit in the entire height range of interbody implants required. The maximum diameter PZT disc was limited to 7 mm and maximum height of PZT insert was 10 mm to ensure even encapsulation above and below the insert. Given these constraints and the desire to maximize the amount of PZT, 15 7×0.4 mm PZT discs were used in the first implant configuration, the 15-disc implants. Seven 7×0.4 mm PZT discs with a 0.4 mm layer of epoxy between each disc, the 7-disc CLACS implants, were chosen for the second implant configuration because of its similar overall height to the 15-disc insert and enhanced power production. To compare the power output for the same volume of PZT to the 7-disc CLACS implants, the final insert configuration had seven 7×0.4 mm PZT discs.

As seen in FIG. 20, the 15-disc implant was able to produce substantially more power across the resistance sweep as compared to the pre and post encapsulated PZT macro fiber implants for similar PZT volumes, despite a 5% decrease in PZT surface area to implant footprint. This increase in power could be attributed to either the PZT discs themselves or the fabrication method used to produce the PZT disc composite implants. The PZT disc composite implants were much more efficient at converting cyclic loads to power. Additionally, the resistance corresponding to maximum power was lower for the 15-disc implant and it did not exhibit the same lack of interface strength, fabrication, or PZT supply chain problems as the macro fiber implants.

Power generation was compared between the 15 disc implant, 7 disc implant, and 7-disc CLACS implant. The addition of the compliant layer did not change the resistance corresponding to maximum power of the implant but did increase the maximum power produced for the same volume of PZT.

The two-way ANOVA for the log of power for the 15-disc, 7-disc, and 7-disc CLACS implants resulted in a significant interaction between implant type and applied resistive load ($p<0.01$). This implies that the amount of power generated by each implant type is highly dependent on the applied resistive load and this effect is largest at resistances below insert impedance, the resistance corresponding to maximum power. The current produced by the piezoelectric implant will need to be rectified to an electronegative signal. This will require a signal conditioning circuit incorporated into the TLIF implant. Smaller electrical components have lower resistances. Therefore, the resistance corresponding to this circuit will most likely take advantage of the compliant layer effect.

For the same PZT volume and ratio of PZT surface area to implant footprint, the 7-disc CLACS implants produced significantly more power than the 7-disc implant for every resistance ($p<0.05$). At 10 MΩ, the resistance corresponding to maximum power, there was a 217% increase in power between the 7-disc and the 7-disc CLACS implants ($p=0.01$).

The two-way ANOVA on the log of power density for the implants resulted in similar power densities ($p>0.05$) across the resistance sweep between the 15-disc and the 7-disc CLACS implants despite the 15-disc implant having more than twice the volume of PZT. This further supports the notion that the compliant layer improves electromechanical coupling per unit volume of PZT material. Additionally, for resistances greater than the impedance of the 15-disc implant, the 7-disc CLACS implant produced more power per unit volume of PZT (FIG. 21). The two-way ANOVA resulted in a significant interaction between implant type and applied resistive load ($p<0.01$). This is likely attributed to the mismatch in insert resistance corresponding to maximum power generated between the implant configurations. While the 7-disc CLACS implants had the greatest overall power density, the maximum power occurred at 10 MΩ as compared to the 15-disc implants that produced maximum power at 4 MΩ. This offset in power exacerbated the difference in power density between these implants.

PZT discs can generate sufficient power to stimulate bone healing. However, many design choices are necessary to develop a TLIF implant with a PZT disc insert. In previous work, a circuit with a resistance of 30 MΩ was used to rectify the power produced by the piezoelectric material to a DC signal. For the three implant types investigated in this study, the power and voltage produced at this resistance level can be seen in Table 3. The 15-disc implant and 7 disc CLACS implant produced significantly more power than the 7-disc implant ($p<0.05$). The power produced by the 15-disc implant and 7-disc CLACS implant were statistically similar. While the 15 disc implant and 7-disc CLACS implant produced the most power, they also produced the most voltage which could add complexity of the implant circuitry. Although the voltage measurements were not the focus of this study, voltage does have a large effect on the electrical components necessary to transform the AC output associated with human motion to an electronegative DC output necessary to stimulate bone growth.

These findings have significant clinical relevance. Lumbar fusion rates remain frustratingly low, and current surgical management has not been able to achieve acceptable outcomes. Recombinant human protein, Rh-BMP-2, currently used off-label in a TLIF interbody, can be used as adjunct therapy to spinal fusion to improve fusion rates. But, it adds significant cost and is associated with several complications, including ectopic bone growth and radiculitis. Other synthetics and bone graft substitutes have not demonstrated high fusion rates. A piezoelectric composite spinal fusion cage offers a potential solution to low fusion rates. It can be placed with standard surgical techniques, has a low risk profile, and will likely be well tolerated by patients.

Conclusions

Three different configurations of PZT disc inserts limited by the size of a 23×10×17 mm TLIF implant successfully produced sufficient power needed to stimulate bone growth using the power generated by the macro fiber implants as the success threshold. Incorporating this technology into a TLIF would be advantageous for patients undergoing lumbar fusion, particularly for the difficult-to-fuse patient population who would benefit from improved healing. As expected, more PZT volume resulted in significantly more power generation. The use of compliant layers between the PZT discs also enhanced power generation. Within a TLIF implant design, PZT discs successfully produced more power as PZT macro fibers for similar ratios of PZT surface area to implant footprint and similar volumes of PZT.

Example 8: Design Considerations for Piezocomposite Materials for Electrical Stimulation in Orthopedic Implants—Compression Poling direction of piezoelectric material is directly related to power generation under loading direction. To better design CLACS for use in various piezoelectric composite orthopedic implants, this study investigates the effect of poling direction of piezoelectric discs on power generation under low frequency compressive loads.

Methods: Three distinct CLACS configurations, radially poled (R), through-thickness poled (T), and alternating R and T (RT) with n=5 in each group were manufactured as described herein. Six pre-poled and electroded 10×0.2 mm PZT discs (SM412, STEMiNC, Doral, FL) were connected electrically in parallel and stacked varying poling direction arrangement (FIGS. 5A-5C). 0.4 mm compliant layers (EPO-TEK 301, Epoxy Technology, Billerica, MA) were adhered between each PZT disc. CLACS were encapsulated in EPO-TEK 301 cylinders. A 1200N preload, followed by cyclic compression at three loads (100, 500, 1000N) was applied at four frequencies (1, 2, 3, 5 Hz) to each CLACS configuration using a biaxial MTS MiniBionix with hydraulic grips. Power generated was calculated from voltage output measured during each load and frequency across a resistance sweep of 20 kΩ-20 MΩ. Maximum power output of each CLACS type as a function of poling direction was compared using a two-way ANOVA and Tukey-Kramer post-hoc analysis ($\alpha=0.05$).

Figure 23:
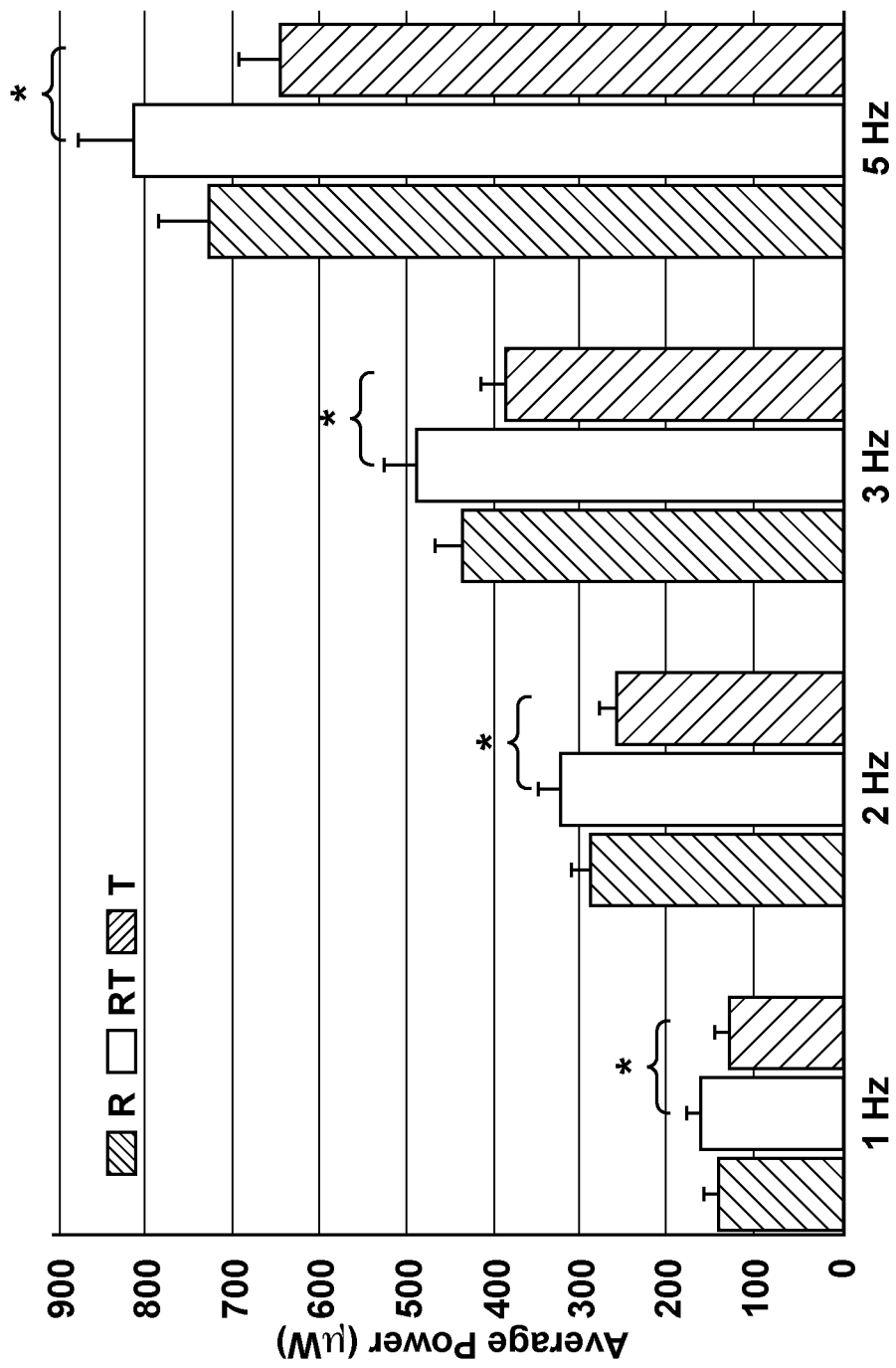
FIG. 23 shows average CLACS power as a function of poling direction and frequency at 1000N and resistance of max power. * represents significant difference (p<0.05).
Figures 24A, 24B:
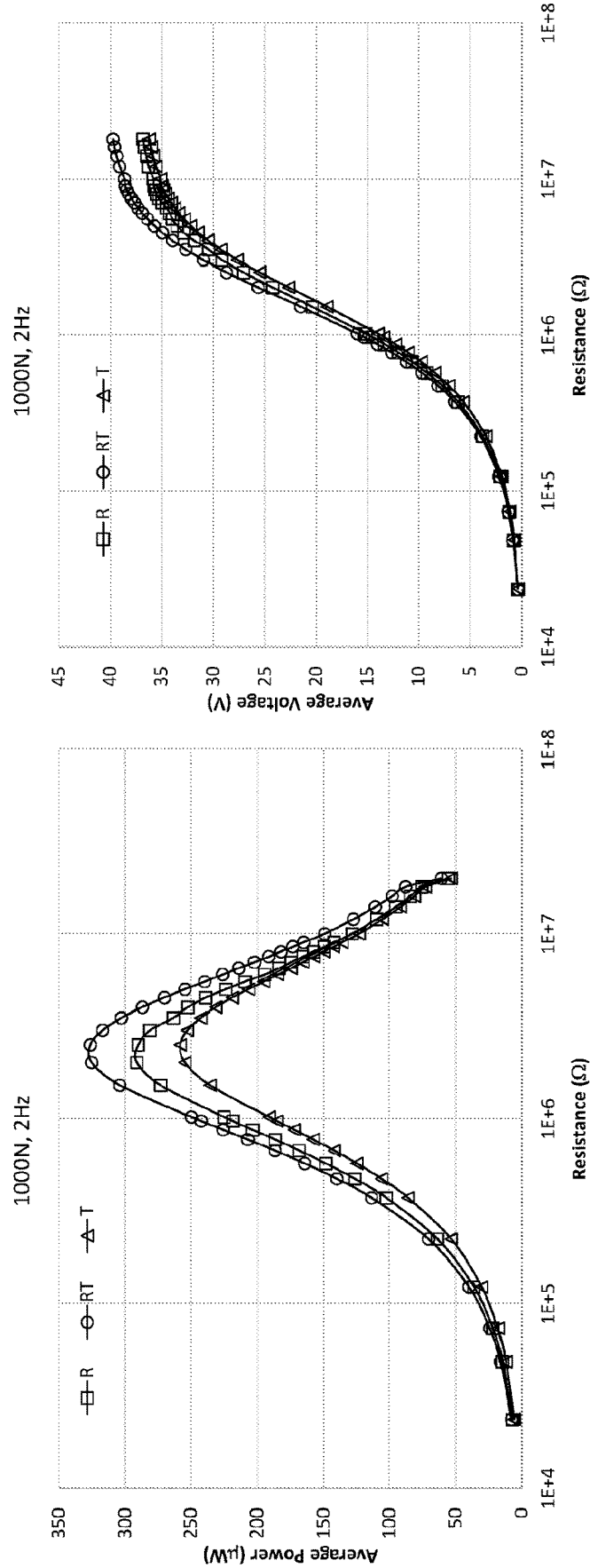
FIG. 24A shows average power as a function of resistance for a 1000N load at 2 Hz for R, RT and T-poled CLACS.
FIG. 24B shows average voltage as a function of resistance for a 1000N load at 2 Hz for R, RT and T-poled CLACS.

Results: The average power generated for each CLACS type as a function of poling direction and frequency is shown in FIG. 23. The compliant layer in the CLACS did increase power output for all groups as compared to stacks with the same poling configurations and no compliant layer. Increased compressive loads and increased frequencies significantly increased power output for all groups ($p<0.05$). At all loads and frequencies, the RT-CLACS produced significantly more power than the T group ($p<0.05$). R—57% increase; RT—95% increase; T—97% increase. There was no significant difference between the R and RT groups. At maximum power there were 1.12 and 1.27-fold increases between the T group and the R and RT groups respectively. These trends held true for all loads, frequencies and resistances tested. The poling direction did not have an effect on source impedance; maximum power occurred at the same resistance for all groups (1000N, 5 Hz, 0.8 MΩ). FIG. 24A shows average power as a function of resistance for a 1000N load at 2 Hz for R, RT and T-poled CLACS. FIG. 24B shows average voltage as a function of resistance for a 1000N load at 2 Hz for R, RT and T-poled CLACS.

Conclusions: The use of CLACS to produce power and generate DC stimulation within an implant, without the use of a battery, can increase non-union healing rates. The power produced by all CLACS types was substantially higher than the necessary power used in clinical DC stimulation devices (140μW). The poling direction of PZT discs did affect power generation across all loads, frequencies and resistances tested.

It will be readily apparent to one of ordinary skill in the relevant arts that other suitable modifications and adaptations to the methods and applications described herein can be made without departing from the scope of any of the embodiments.

All references, patents and patent applications cited herein are incorporated by reference in their entireties for all purposes.

It is to be understood that while certain embodiments have been illustrated and described herein, the claims are not to be limited to the specific forms or arrangement of parts described and shown. In the specification, there have been disclosed illustrative embodiments, and although specific terms are employed, they are used in a generic and descriptive sense only and not for purposes of limitation. Modifications and variations of the embodiments are possible in light of the above teachings. It is therefore to be understood that the embodiments may be practiced otherwise than as specifically described.

What is claimed is:

1. A stacked piezoelectric energy harvester, comprising:
    a. a first piezoelectric element layer;
    b. a first compliant layer positioned adjacent the first piezoelectric element layer; and
    c. a second piezoelectric element layer positioned adjacent the first compliant layer,
    wherein a ratio of a volume of the first piezoelectric element layer and/or a volume of the second piezoelectric element layer, to a volume of the first compliant layer is between about 1:8 volume piezoelectric:volume compliant to about 8:1 volume piezoelectric:volume compliant, or
    wherein a ratio of a thickness of the first piezoelectric element layer and/or a thickness of the second piezoelectric element layer, to a thickness of the first compliant layer is between about 1:8 thickness piezoelectric:thickness compliant to about 8:1 thickness piezoelectric:thickness compliant; and
    wherein the first piezoelectric element layer is poled in a radial direction and the second piezoelectric element layer is poled in a through-thickness direction; and, wherein the stacked energy harvester is configured to withstand a minimum load of at least 500 N.

2. The stacked piezoelectric energy harvester of claim 1, wherein the first piezoelectric element layer comprises lead zirconium titanate, barium titanate or polyvinylidene difluoride (PVDF).

3. The stacked piezoelectric energy harvester of claim 1, wherein the first compliant layer comprises a polymer.

4. The stacked piezoelectric energy harvester of claim 3, wherein the polymer is an epoxy, a polyethylene, or a polyether ether ketone (PEEK).

5. The stacked piezoelectric energy harvester of claim 1, wherein the first compliant layer has a bulk modulus that is at least 50% less than a bulk modulus of the first piezoelectric element layer and/or the second piezoelectric element layer.

6. The stacked piezoelectric energy harvester of claim 1, further comprising a polymer encapsulating the stacked piezoelectric energy harvester.

7. The stacked piezoelectric energy harvester of claim 1, wherein the ratio of the volume of the first piezoelectric element layer and/or the volume of the second piezoelectric element layer, to the volume of the first compliant layer is between about 1:4 volume piezoelectric:volume compliant to about 1:8 volume piezoelectric:volume compliant.

8. The stacked piezoelectric energy harvester of claim 1, wherein the first compliant layer has a thickness of about 0.2 mm to about 8 mm.

9. The stacked piezoelectric energy harvester of claim 1, further comprising one or more additional piezoelectric element layers and one or more additional compliant layers.

10. The stacked piezoelectric energy harvester of claim 9, wherein each of the compliant layers has a thickness within about 40% of each other.

11. The stacked piezoelectric energy harvester of claim 9, wherein each of the compliant layers has a thickness within about 10% of each other.

12. A method of providing power generation from the stacked piezoelectric energy harvester of claim 1, comprising loading the stacked piezoelectric energy harvester with a load of at least about 500 N.

13. The method of claim 12, wherein the power generation is provided to a tissue-stimulating implant of a patient.

14. The method of claim 13, wherein the tissue-stimulating implant is a spinal implant.

15. A stacked piezoelectric energy harvester, comprising:
    alternating layers of:
    N compliant layers; and
    N–1 piezoelectric element layers;
    wherein the compliant layers and the piezoelectric element layers are adjacent one another,
    wherein N is a whole integer between 3 and 20, and
    wherein a ratio of a volume of at least one of the piezoelectric element layers, to a volume of at least one of the compliant layers is between about 1:8 volume piezoelectric:volume compliant to about 8:1 volume piezoelectric:volume compliant, or
    wherein a ratio of a thickness of at least one of the piezoelectric element layers, to a thickness of at least one of the compliant layers is between about 1:8 thickness piezoelectric:thickness compliant to about 8:1 thickness piezoelectric:thickness compliant; and
    wherein the stacked piezoelectric energy harvester has a total thickness in the range of 11 mm to 17 mm.

16. The stacked piezoelectric energy harvester of claim 15, wherein the piezoelectric element layers are electrically connected to each other.

17. The stacked piezoelectric energy harvester of claim 15, wherein the piezoelectric element layers comprise lead zirconium titanate, barium titanate or polyvinylidene difluoride (PVDF).

18. The stacked piezoelectric energy harvester of claim 15, wherein the compliant layers comprise a polymer.

19. The stacked piezoelectric energy harvester of claim 18, wherein the polymer is an epoxy, a polyethylene, or a polyether ether ketone (PEEK).

20. The stacked piezoelectric energy harvester of claim 15, wherein each of the compliant layers has a bulk modulus that is at least 50% less than a bulk modulus of each of the piezoelectric element layers.

* * * * *